United States Patent [19]

Foglio et al.

[11] Patent Number: 4,558,042

[45] Date of Patent: Dec. 10, 1985

[54] β-LACTAM-CONTAINING ANTIBACTERIAL AGENTS AND β-LACTAMASE INHIBITORS

[75] Inventors: Maurizio Foglio; Giovanni Franceschi; Cosimo Scarafile; Federico Arcamone; Aurora Sanfilippo, all of Milan, Italy

[73] Assignee: Farmitalia Carlo Erba S.p.A., Milan, Italy

[21] Appl. No.: 595,336

[22] Filed: Mar. 30, 1984

Related U.S. Application Data

[63] Continuation of Ser. No. 261,247, May 6, 1981, Pat. No. 4,482,565, which is a continuation-in-part of Ser. No. 123,787, Feb. 22, 1980, abandoned, which is a continuation-in-part of Ser. No. 66,333, Aug. 14, 1979, abandoned.

[51] Int. Cl.$^4$ ............... C07D 499/00; A61K 31/425
[52] U.S. Cl. ................... 514/192; 514/195; 260/245.2 R; 260/239 A
[58] Field of Search ............ 260/245.2 R; 424/270; 514/195, 192

[56] References Cited

U.S. PATENT DOCUMENTS 4,256,733  3/1981  Barth ..................... 260/245.2 R
4,423,055 12/1983  McCombie ................ 260/245.2 R
4,482,565 11/1984  Foglio et al. ............ 260/245.2 T
4,485,110 11/1984  Osborne et al. .......... 424/270

Primary Examiner—Nicholas S. Rizzo

[57] ABSTRACT

There are disclosed β-lactam-containing compounds of the formula:

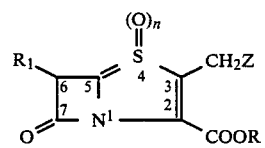

where R is hydrogen, lower alkyl, trichloroethyl, acetonyl, benzyl, substituted benzyl, phenyl, substituted phenyl, benzidryl or a residue that will undergo metabolic activation "in vivo" and have favorable pharmacokinetic properties; $R^1$ is a hydrogen atom, lower alkyl, lower alkoxy, cycloalkyl, or hydroxyalkyl, with the alcoholic function of the hydroxyalkyl being free or protected; Z is hydrogen, halogen, hydroxy, amino, carbamoyloxy, mercapto, pyridinium, $OR^2$, $OCOR^2$, $NHCOR^2$, or $SR^3$ wherein each of $R^2$ and $R^3$ is any of lower alkyl, aryl, or a heterocyclic ring, each of which may be substituted or unsubstituted, and n is 0 or 1. The compounds have broad spectrum antibacterial activity and β-lactamase inhibiting activity. Processes for the production of the β-lactam-containing compounds and various intermediates in the production of those compounds are also disclosed.

6 Claims, No Drawings

β-LACTAM-CONTAINING ANTIBACTERIAL AGENTS AND β-LACTAMASE INHIBITORS

CROSS-REFERENCE TO RELATED APPLICATIONS

This application is a continuation of Ser. No. 261,247, filed May 6, 1981, now U.S. Pat. No. 4482965 which is a continuation-in-part of Ser. No. 123,787, filed Feb. 22, 1980, now abandoned which is a continuation-in-part of Ser. No. 66,333, filed Aug. 14, 1979, now abandoned.

GENERAL DESCRIPTION OF THE INVENTION

This invention relates to β-lactam-containing compounds to processes for their preparation, and to compositions containing them.

More particularly, the present invention relates to penem-carboxylic acids of the formula:

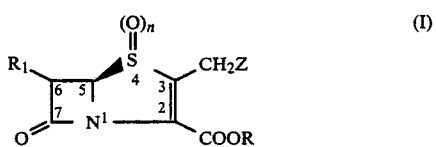

wherein R is a hydrogen atom, lower alkyl; 2,2,2-trichloroethyl, acetonyl, benzyl, p-nitrobenzyl, p-methoxybenzyl, phenyl, p-nitrophenyl, benzyhydryl, or a residue known to undergo metabolic activation "in vivo" and having favorable pharmacokinetic properties, including acetoxymethyl, pivaloyloxymethyl or phthalidyl or a group of the formula

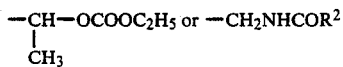

in which $R^2$ is alkyl having from 1 to 5 carbon atoms or aryl; Z is a hydrogen or halogen atom, hydroxy, amino, carbamoyloxy, mercapto, pyridinium, or a group of the formula $OR^3$, $OCOR^3$, $NHCOR^3$, and $SR^4$ wherein each of $R^3$ and $R^4$ is lower alkyl, aryl, or a heterocyclic ring, each of which may be substituted or unsubstituted; and $R^1$ is a hydrogen atom, lower alkyl, lower alkoxy, cycloalkyl or hydroxyalkyl (preferably lower hydroxyalkyl), the alcoholic function of the hydroxyalkyl being free or protected, the protecting group being preferably p-nitrobenzyloxycarbonyl or dimethyl-t-butyl-silyl, and n is 0 or 1. The substituent in the 6 position has the α-configuration as well as the β-configuration. The α-configuration is preferred.

Examples of residues included within the definition of R that are known to undergo metabolic activation "in vivo" and have favorable pharmacokinetic properties, include acetoxymethoxy, pivaloyloxymethyl, and phthalidyl and groups of the formulae

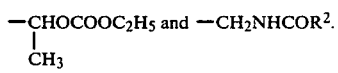

For purposes of the instant application, the term "lower alkyl" is defined as an alkyl having from 1 to 5 carbon atoms, and include methyl, ethyl, propyl, isopropyl, butyl, isobutyl, tert.-butyl, and pentyl. Preferred lower alkyl moieties are methyl, ethyl, and tert.-butyl.

The term "aryl" includes phenyl and benzyl; either unsubstituted or substituted with any of hydroxy, methyl, methoxy, halogen, amino, and nitro groups. The substituted compounds can be prepared in conventional ways known in the art.

Representative values of $R^1$ include methy, ethyl, methoxy, 1-hydroxyethyl, and 1-(p-nitrobenzyloxy-carbonyloxy)-ethyl.

$R^3$ and $R^4$, when heterocyclic, are preferably a 5- or 6-membered heterocyclic ring residue having from 1 to 4 or 1 to 5 carbon atoms respectively and up to 4 or 5 heteroatoms respectively, wherein the heteroatoms are selected from the group consisting of nitrogen, oxygen, and sulfur. The heterocyclic ring residue can be unsubstituted or substituted; when substituted, the substituent is selected from the group consisting of lower alkyl, lower hydroxyalkyl, lower alkoxy, halogen, hydroxy, amino, and nitro. The heterocyclic ring residues are preferably (a) monocyclic, five-membered, diaza, triaza, tetraza-, thiaza, thiadiaza-, oxaza- or oxadiazacyclic radicals, either unsubsti-tuted or substituted with the above-mentioned substituents, or (b) monocyclic, six-membered, monoazacyclic or diazacylic radicals either unsubstituted or substituted with the above-mentioned substituents. Preferred examples of the heterocyclic ring residues used in the present invention are imidazol-2-yl; 1,2,3-triazol-5-yl; 1-methyltetrazol-5-yl; thiazol-2-yl, thiadiazol-2-yl; 1,2,3,4-thiatriazol-5-yl; oxazol-5-yl; 3-methylisoxazol-5-yl; 1,2,4-oxadiazol-5-yl, and pyrazinyl. Particularly preferred heterocyclic residues are 5-methyl-1,3,4-thiadiazol-2-yl; 1-methyl-tetrazol-5-yl; 1,2,3-triazol-5-yl, and pyrazinyl.

The term "lower alkoxy" refers to an alkoxy group having from 1 to 5 carbon atoms, for example, methoxy, ethoxy, propoxy, isopropoxy, butoxy, isobutoxy, tert.-butoxy, and pentoxy.

The cycloalkyl moieties used in the present application have from 3 to 7 carbon atoms and include cyclopropyl, cyclobutyl, cyclopentyl, cyclohexyl, cyclopropylmethyl, and cyclobutylmethyl.

The lower hydroxyalkyl groups include, for example, hydroxymethyl, 1-hydroxyethyl, 2-hydroxyethyl, 1-hydroxypropyl, 2-hydroxypropyl, and 3-hydroxypropyl.

The compounds of the present invention possess a wide spectrum of antibacterial activity and also have β-lactamase-inhibiting activity. It should be pointed out that the stereochemistry at $C_5$ of the novel β-lactam-containing compounds, including the intermediates for their preparation, is identical to the naturally-occurring penicillins and cephalosporins.

Pharmaceutically acceptable salts of penem-carboxylic acids of formula (1) including sodium, postassium, benzathin, procaine, and like salts usually formed with penicillins and cephalosporins, are also within the scope of the invention. The invention also includes processes of preparing the compounds of formula (1), intermediates therefor, and pharmaceutically acceptable compositions containing the compounds of formula (1) in admixture with the usual carriers for oral and parenteral administration. The following diagram illustrates the preparation of the compounds of formula (1) according to the invention.

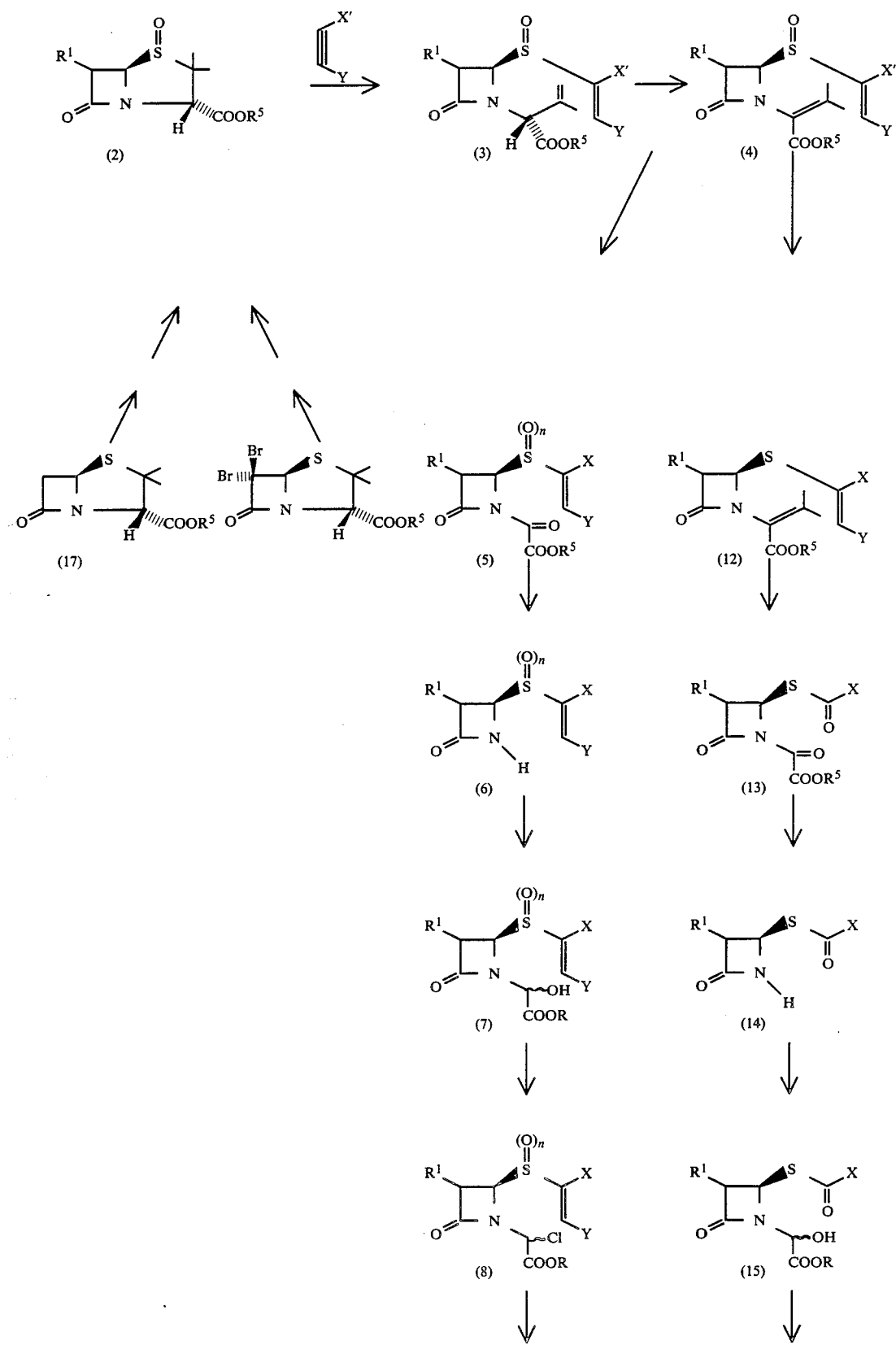

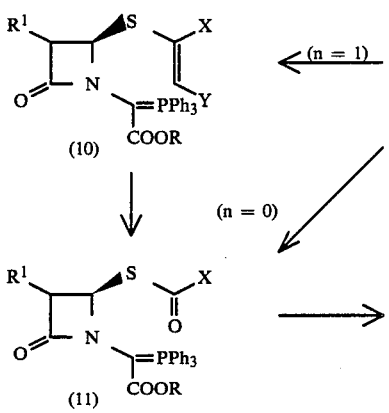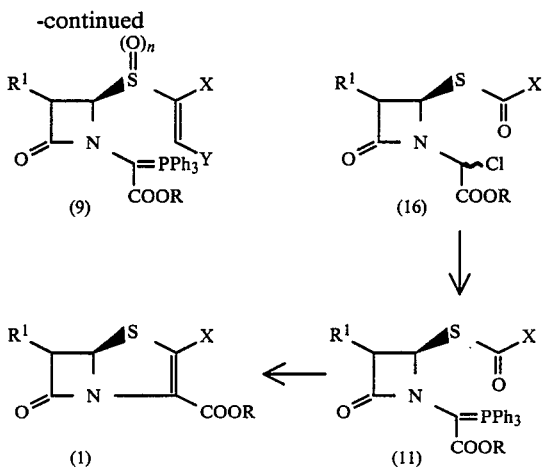

When $R^1$ is hydrogen, compounds of formula (2) are prepared starting from (SR) 6-aminopenicillanic acid (6-APA), following the widely-known general procedure (see CIGNARELLA et al., Journal of Organic Chemistry, 27, 2668 and EVRARD et al., Nature, 201, 1124). When $R^1$ is lower alkyl, cycloalkyl, or hydroxyalkyl, the $R^1$ group can be introduced according to the procedure of Di Ninno et al., Journal of Organic Chemistry, 42, 2960 (1977). When $R^1$ is lower alkoxy, the $R^1$ group can be introduced in the 6-position starting from 6-APA in accordance with the procedure of Hauser et al., Helv. Chem. Acta, 50; 1327 (1967) and Giddings et al., Tetrahedran Letters, 11, 995 (1978).

Alternatively, compounds of general formula (2) in which $R^1$ is H can be converted to compounds of the general formula (2) in which $R^1$ is lower alkyl, cycloalkyl, or hydroxyl by introducing the substituent into the 6-position using a strong base as illustrated in the following examples.

Compounds of formula (2) in which $R^1$ is lower alkyl, cycloalkyl, or hydroxyalkyl can be prepared also starting from a suitable ester of the penicillanic acid S-oxide, as illustrated in the following examples. The substitution of the 6 position is stereospecifically directed to the 6α derivatives.

The ester of penicillanic acid S-oxide (2) wherein $R^5$ is an alkyl group e.g., $C_1$–$C_8$ alkyl, and $R^1$ is as above defined, may be heated in an inert solvent, such as benzene or toluene, usually at a temperature of from 70° C. to 140° C., with a suitable acetylenic derivative of the general formula X′C≡CY wherein X′ is a group of the formula $CH_2Z'$ wherein Z′ is a hydrogen or halogen atom, hydroxy, amino, carbamoyloxy, or a group of the formula $OR^3$, $OCOR^3$, or $NHCOR^3$ where $R^3$ is lower alkyl, aryl or a heterocyclic ring, any of $R^3$ being optionally substituted, and Y is hydrogen atom, lower alkyl, cyano or a group of the formula $COOR^5$ or $CH_2Z'$ wherein $R^5$ and Z′ have the meanings given above.

In the compounds of formula (3), X′, when different, can be converted to a group X, wherein X is a group of the formula $CH_2Z$ wherein Z has the meaning given to it supra by means of the widely-known substitution reactions, one example of which is given in the following examples. The trapped compound of formula (3) may be isomerized by using a base into the compound of formula (4) which can be converted to the final compound of formula (1) in two different ways. In one way, the compound of formula (4) may be ozonized selectively on the isopropenyl double bond to give a compound of formula (5) wherein n=1, which may be reduced to a compound of formula (5) wherein n=0 with suitable reducing agents such as phosphorous tribromide or sodium iodide in acetyl chloride and subsequently hydrolyzed to a compound of formula (6) where n=0 in mild basic conditions or on silica gel. Condensation with a suitable ester of glyoxylic acid gives a compound of formula (7) where n=0, which may be transformed into the chloroderivative of formula (8) wherein n=0 by means of a chlorinating agent such as thionyl chloride and pyridine, and then into the phosphorane of formula (9) where n=0. Moreover, the same group of reactions is also performed starting from the unexpected compounds of formula (6) where n=1 which is stable when Y is not a strong withdrawing group. In the case involving the compound of formula (9) where n=0, the compound may be selectively ozonized as a phosphonium salt in acidic conditions to give the compound of formula (11), which is cyclized to the compounds of formula (1), simply by heating in an inert solvent, such as toluene, at a temperature of from 50° C. to 140° C.

In the case of a compound of formula (9) where n=1, the compound must be reduced to the compound of formula (10) and subsequently ozonized to the compound of formula (11), which gives in turn the compound of formula (1).

In the second way, the compound of formula (4) may be reduced under the usual conditions to give the compound of formula (12), which is ozonized on both double bonds to give the compound of formula (13) and, after hydrolysis, the compound of formula (14). Following the same procedure as in the previous way, glyoxylation of the compound of formula (14) gives the compound of formula (15), which may be transformed to the chloroderivative of formula (16) and then to the phosphorane of formula (11), which is a common intermediate for both ways.

When $R^1$ is hydroxyalkyl, the reaction sequence is preferably carried out with the alcoholic function protected.

Compounds of formula (1) in which R is a hydrogen atom can be obtained by hydrolysis or hydrogenolysis of the corresponding esterified comound. Compounds of formula (1) in which n=1 are easily prepared starting from compounds of formula (1) in which n=0, following the widely known oxidation processes. Peracids can be advantageously used; m-chlorperbenzoic acid and peracetic acid are preferred. The processes illustrated hereinabove are within the scope of the invention.

A series of tests was carried out in vitro to compare the activities of (5R)-acetoxymethyl-2-acetoxymethyl-2-penem-3-carboxylate (Laboratory code FCE/20077/B40/341), (5R) acetoxymethyl-2-[1-methyl-1H-tetrazol-5-yl)-thiomethyl]-2-penem-3-carboxylate (compound A), three reference compounds (ampicillin, cefoxitin, and thienamycin), and compound 387, which is (5R)-2-acetoxymethyl-6-(1-hydroxyethyl 1-2-penem-3-carboxylic acid. The acetoxymethoxy ester of compound 387 is prepared in Example 51 and the sodium salt of the acid is prepared in Example 98 infra). Table 1 below reports the results of the above assays as MIC (minimal inhibitory concentration).

EXAMPLE 1

4β-Vinylthio-[1,2-diacetoxymethyl]-1-[methoxycarbonyl-2-methyl-2-propenyl]-azetidin-2-one-S-oxide
Reaction (2)–(3)

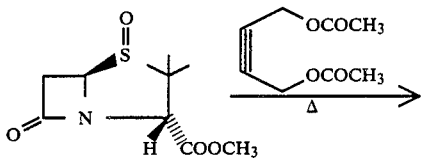

TABLE 1

| Strains | MIC µg/ml | | | | | |
|---|---|---|---|---|---|---|
| | FCE/20077/B40/341 | Compound A | Ampicillin | Cefoxitin | Thienamycin | 387 |
| *Staphylococcus aureus* 209P+ | 0.39 | 0.39 | ≦0.19 | 0.78 | ≦0.39 | 0.095 |
| *Staphylococcus aureus* 153° | 1.56 | 0.78 | 1.56 | 0.78 | — | 0.045 |
| *Staphylococcus aureus* PV2 | 0.39 | 0.78 | ≦0.19 | 0.78 | — | — |
| *Staphylococcus aureus* Smith+ | ≦0.19 | 0.39 | ≦0.19 | 0.78 | — | 0.045 |
| *Streptococcus pyogenes* | 3.12 | 0.78 | 3.12 | 1.56 | — | 0.19 |
| *Escherichia coli* B+ | 1.56 | 0.78 | 0.39 | 1.56 | 0.78 | 0.78 |
| *Escherichia coli* V14 | 1.56 | 0.78 | 1.56 | 3.12 | — | — |
| *Escherichia coli* V23 | 3.12 | 0.78 | 3.12 | 12.5 | — | — |
| Enterobacter sp V19 | 12.5 | >100 | >100 | 12.5 | — | — |
| *Klebsiella pneumoniae* ATCC 10031 | — | 3.12 | 50 | 0.78 | — | — |
| Klebsiella sp. R2 | 25 | — | 50 | 12.5 | — | — |
| *Proteus vulgaris* V15 | 3.12 | 6.25 | 1.56 | 0.78 | — | — |
| *Proteus mirabilis* V15 | 0.39 | 0.78 | ≦0.19 | 0.78 | — | — |
| *Proteus mirabilis* 525 | 3.12 | 0.78 | 0.39 | 1.56 | — | — |
| *Shigella flexneri* | 0.39 | 0.39 | ≦0.19 | 0.78 | — | — |
| *Pseudomonas aeruginosa* | 3.12 | 0.39 | 25 | 6.25 | 12.5 | 1.56 |
| *Salmonella typhimurium* | 1.56 | 0.78 | 0.78 | 3.12 | — | 0.39 |
| *Salmonella panamae* F15 | 1.56 | 0.78 | 0.78 | 1.56 | — | — |
| *Salmonella Saint Paul* F20 | 1.56 | 0.78 | 0.78 | 3.12 | — | — |
| *Salmonella derby* F 14 | 3.12 | 0.78 | 0.78 | 3.12 | — | — |
| *Salmonella montevideo* F16 | 3.12 | 0.78 | 0.78 | 3.12 | — | — |
| *Escherichia coli* B Cef R° | — | — | >100 | >100 | 12.5 | 25 |
| *Escherichia coli* RGN 238° | — | — | >100 | 3.12 | 0.36 | 0.78 |
| *Escherichia coli* P 453° | — | — | >100 | 1.56 | 0.78 | 0.78 |
| *Escherichia coli* R 997° | — | — | >100 | 6.25 | 0.36 | 0.78 |
| *Escherichia coli* R 57 B° | — | — | 25 | 1.56 | — | 0.78 |
| *Escherichia coli* RP 1° | — | — | >100 | 1.56 | 0.36 | 0.39 |
| *Escherichia coli* R 46° | — | — | 25 | 1.56 | — | 0.78 |
| *Escherichia coli* R 6 K° | — | — | >100 | 3.1 | 0.78 | 0.78 |
| *Pseudomonas aeruginosa* F1+ | — | — | >100 | 6.25 | 12.5 | 1.56 |
| *Pseudomonas aeruginosa* ATCC 2598+ | — | — | >100 | >100 | — | >25 |
| *Klebsiella aerogenes* ATCC 1082 E° | — | — | >100 | 6.25 | 1.56 | 1.56 |
| *Klebsiella pneumoniae* ATCC 10031+ | — | — | 25 | 0.78 | 1.56 | 0.78 |
| *Enterobacter cloacae* P 99° | — | — | >100 | 100 | — | 3.12 |
| *Enterobacter cloacae* 214° | — | — | >100 | >100 | — | 12.5 |
| *Salmonella abortivoequina*+ | — | — | 0.19 | 0.78 | — | 0.19 |
| *Salmonella Typhimurium*+ | — | — | 0.78 | 1.56 | — | 0.39 |
| *Proteus mirabilis*+ | — | — | >100 | 1.56 | — | 0.39 |

+ = Collection strains
° = Strains producers of various types of β-Lactamases

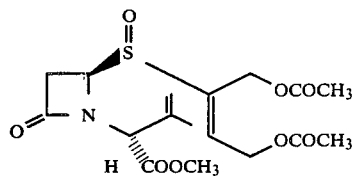

A solution of 2.0 g of methylpenicillinate S-oxide and 2.8 g of butyndiol diacetate in 40 ml of toluene was heated at refluxing temperature for 24 hrs. The title compound can be purified by column chromatography on silica gel eluting with 96:4 dichloromethane-ethyl acetate. There was obtained 1.4 g of 4β-vinylthio-[1,2-diacetoxymethyl]-1-[1-methoxycarbonyl-2-methyl-2-propenyl]-azetidin-2-one-S-oxide.
PMR (CDCl$_3$):

The following examples are illustrative but should not be regarded as limiting the invention.

2.03 δ

(s, CH₃—C(=O)—), 2.15 and 2.20 δ (two s, 2CH₃CO),
2.88 δ (dd, Jgem—14 Hz, Jvic cis=4 Hz, C—3—Hα)
3.38 δ (dd, Jgem—14 Hz, Jvic trans—2 Hz, C—3—Hβ)
3.83 δ (s, CH₃O)
4.88 δ (d, Jvic—6 Hz,

CH₂—C(=)
  |
  (H)
—N
  CH
  |
  COO 4.92 δ (broad s,

CH₂—C(=)
  |

4.93–5.33 δ (m, =CH₂ and
5.32 δ (dd, Jvic=4 and 2 Hz, C—4—H),
6.47 δ (t, Jvic—6 Hz,

=C—C(H₂))
  |
  H

EXAMPLE 2

4β-Vinylthio-[1,2-diacetoxymethyl]-1-[methoxycarbonyl-2-methyl-1-propenyl]-azetidin-2-one-S-oxide Reaction (3)-(4)

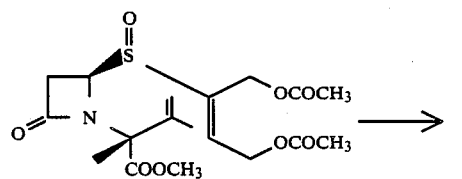

1.7 g of 4β-vinylthio-[1,2-diacetoxymethyl]-1-[1-methoxycarbonyl-2-methyl-2-propenyl]-azetidin-2-one-S-oxide were dissolved in 80 ml of dichloromethane; 0.5 ml of triethylamine were added and the solution was left for a few hours at room temperature. After evaporating the solvent, the title compound was obtained pure in quantitative yields.
PMR (CDCl₃):
2.13 (9H) and 2.32 (3 h) δ (two s, 2 CH₃CO and 2

CH₃—C=)
  |

2.92 δ (dd, Jgem—15 Hz, Jvic cis—5 Hz, C—3—Hα),
3.38 δ (dd, Jgem—15 Hz, Jvic trans—2.5 Hz, C—3—Hβ)
3.82 δ (s, CH₃O),
4.88 δ (d, Jvic—6.5 Hz,

CH₂—C=)
  |
  (H)

4.92 δ (s, CH₂—C≡)
5.15 δ (dd, Jvic=5 and 2.5 Hz, C—4—H),
6.50 δ (t, Jvic 6.5 Hz, =

C—(H₂))
|
H

EXAMPLE 3

4β-Vinylthio-[1,2-diacetoxymethyl]-1-[methoxyoxaloyl-azetidin-2-one-S-oxide Reaction (4)-(5)

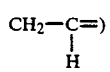

2.0 g of 4βp-vinylthio-[1,2-diacetoxymethyl]-1-[1-methoxycarbonyl-2-methyl-1-propenyl]-azetidin-2-one-S-oxide, were dissolved in 150 ml of dichloromethane and, after cooling at −78° C., a flow of ozone in oxygen was bubbled into the cooled solution until a slightly blue color appeared. The solution was warmed to room temperature, shaken with an aqueous solution of Na₂S₂O₅, and dried over Na₂SO₄. The resulting organic phase gave, after evaporating the solvent "in vacuo", 1.4 g of the title compound.
PMR (CDCl₃):
2.05 and 2.08 δ (two s, 2 CH₃CO),
3.03 δ (dd, Jgem=17 Hz, Jvic cis=5.5 Hz, C—3—Hα),
3.50 δ (dd, Jgem=17 Hz, Jvic trans=3 Hz, C—3—Hβ),
3.90 δ (s, CH₃O),
4.82 δ (d, Jvic=6.5 Hz,

CH₂—C=)
  |
  H 4.90 δ (s, CH₂—C=), 5.32 δ (dd, Jvic=5.5 and 3 Hz, C—4—H),
6.47 δ (t, Jvic=6.5 Hz,

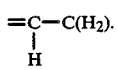

IR (CH₂Cl₂):
  1830 cm⁻¹ β-lactam C=O;
  1750 cm⁻¹ esters C=O;
  1715 cm⁻¹ amide C=O.

EXAMPLE 4

4β-Vinylthio-[1,2-diacetoxymethyl]-1-methoxyoxaoyl-azetidin-2-one Reaction (5)

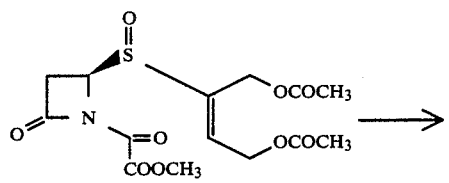

A solution of 1.4 g of 4β-vinylthio-[1,2-diacetoxymethyl]-1-methoxy-oxaloyl-azetidin-2-one-S-oxide in 10 ml of anhydrous dimethylformamide was cooled at −25° C. and 0.9 ml of phosphorous tribromide were added thereto. After 10 minutes, the mixture was diluted with ethyl acetate and washed twice with a saturated solution of NaHCO₃. After drying over Na₂SO₄ and evaporating the solvent, 0.9 g of the title compound were obtained.
PMR (CDCl₃):
  2.07 δ (s, 2 CH₃CO),
  3.17 δ (dd, Jgem=19 Hz, Jvic trans=3.5 Hz, C—3—Hβ),
  3.65 δ (dd, Jgem=19 Hz, Jvic cis=5 Hz, C—3—Hα),
  3.90 δ (s, CH₃O),
  4.73 δ (d, Jvic—6.5 Hz,

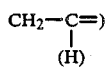

4.88 δ (broad s,

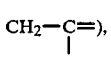

5.52 δ (dd, Jvic=5 and 3.5 Hz, C—4—H),
  6.25 δ (t, Jvic=6.5 Hz, =

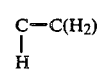

IR (CHCl₃):
  1815 cm⁻¹ β-lactam C=O;
  1745 cm⁻¹ esters C=O;
  1710 cm⁻¹ amide C=O.

EXAMPLE 5

4β-Vinylthio-[1,2-diacetoxymethyl]-azetidin-2-one Reaction (5)-(6)

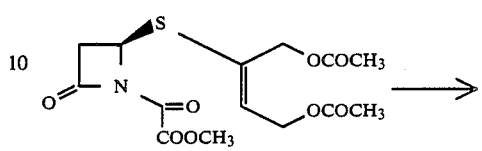

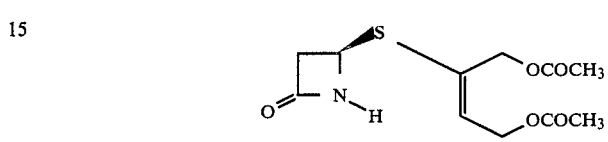

1.5 g of 4β-vinylthio-[1,2-diacetoxymethyl]-1-methoxyoxaloylazetidin-2-one were dissolved in 100 ml of methanol and a few grams of silica gel were added under stirring. After one hour, the silica gel was filtered off and the methanolic solution evaporated to give 0.8 g of 4β-vinylthio-[1,2-diacetoxymethyl]-azetidin-2-one.
PMR (CDCl₂):
  2.25 δ (s, 2 CH₃CO),
  2.98 δ (dd, Jgem=15 Hz, Jvic trans=2 Hz, C—3—Hβ),
  3.48 δ (dd, Jgem=15 Hz, Jvic cis—4.5 Hz, C—3—Hα),
  4.78 δ (d, Jvic=7 Hz,

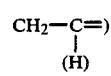

4.87 δ (s, CH₂—C),
  5.03 δ (dd, Jvic=4.5 and 2 Hz, C—4—H),
  6.02 δ (t, Jvic=7 Hz,

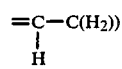

7.13 δ (broad s, N—H).
IR (CHCl₃):
  1770 cm⁻¹ β-lactam C=O;
  1740 cm⁻¹ esters C=O.

EXAMPLE 6

4β-Vinylthio-[1,2-diacetoxymethyl]-azetidin-2-one-S-oxide Reaction (5)-(6)

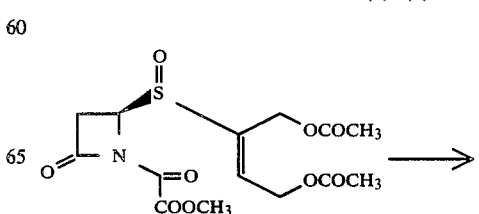

-continued

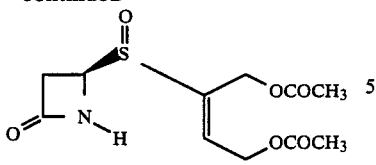

0.8 g of 4β-vinylthio-[1,2-diacetoxymethyl]-1-methoxyoxaloylazetidin-2-one-S-oxide were dissolved in 80 ml of methanol and a few grams of silica were added under stirring. After one hour the silica gel was filtered off and 0.5 g of 4β-vinylthio-[1,2-diacetoxymethyl]-azetidin-2-one-S-oxide were obtained after evaporation of the solvent.

PMR (CDCl$_3$):
2.13 δ (s, 2 CH$_3$CO),
3.0–3.3 δ (m, 2 protons at C—3),
4.70 δ (m, C—4—H),
4.88 δ (d, Jvic=6 Hz,

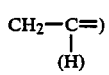

4.93 δ (s, CH$_2$—C=)
6.53 δ (t, Jvic=6 Hz,

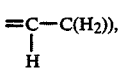

7.23 δ (s, NH).
IR (CHCl$_3$):
1790 cm$^{-1}$ β-lactam C=O;
1745 cm$^{-1}$ esters C=O.

EXAMPLE 7

4β-Acetylglycolylthio-1-acetoxymethyloxyoxaloyl-azetidin-2-one Reaction (12)–(13)

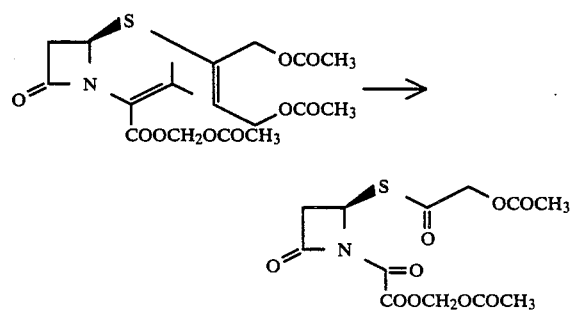

0.8 g of 4β-vinylthio-[1,2-diacetoxymethyl]-1-[1-acetoxymethyloxycarbonyl-2-methyl-1-propenyl]-azetidin-2-one were dissolved in 80 ml of dichloromethane, cooled at −78° C. and a flow of ozone in oxygen was bubbled into the cooled solution until a blue color appeared. The solution, after shaking it with an aqueous solution of Na$_2$S$_2$O$_5$, was dried over Na$_2$SO$_4$ to give 0.45 g of the title compound.

PMR (CDCl$_3$):
2.10 and 2.13 δ (two s, 2 CH$_3$CO)
3.20 δ (dd, Jgem=17 Hz, Jvic trans=3.5 Hz, C—3—Hβ),
3.77 δ (dd, Jgem=17 Hz, Jvic cis=5.5 Hz, C—3—Hα),
4.73 δ (s, —CO—CH$_2$—OCO—),
5.73 δ (dd, Jvic 5.5 and 3.5 Hz, C—4—H),
5.87 δ (s, COO—CH$_2$—OCO).

EXAMPLE 8

4β-Acetylglycolylthio-azetidine-2-one Reaction (13)–(14)

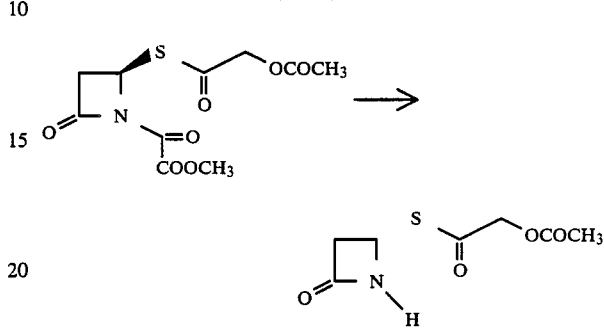

0.6 g of 4β-acetylglycolylthio-1-methoxyoxaloyl-azetidin-2-one were dissolved in 100 ml of methanol and a few grams of silica gel were added as the solution was stirred. After one hour, the silica gel was filtered off and the resulting solution gave, after evaporation of the solvent, 0.35 g of the title compound.

PMR (CDCl$_3$):
2.20 δ (s, CH$_3$CO),
3.03 δ (dd, Jgem=16 Hz, Jvic trans=2.5 Hz, C—3—Hβ),
3.50 δ (dd, Jgem=16 Hz, Jvic cis=4.5 Hz, C—3—Hα),
4.77 δ (s, —CO—CH$_2$—OCO—),
5.32 δ (dd, Jvic=4.5 e 2.5 Hz, C—4—H),
6.40 δ (broad s, NH).

EXAMPLE 9

4β-Vinylthio-[1,2-diacetoxymethyl]-1-[1-acetoxymethyloxycarbonyl-1-hydroxymethyl]-azetidin-2-one Reaction (6)–(7)

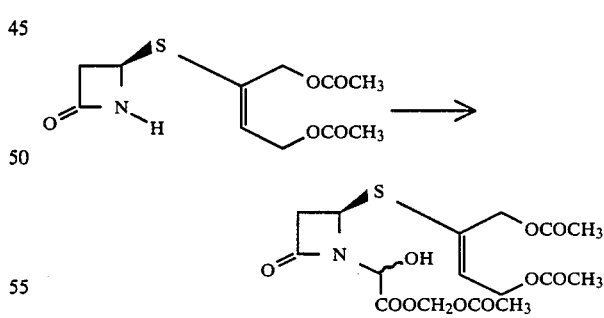

0.7 g of acetoxymethyl-glyoxylate (freshly prepared by the ozonolysis of diacetoxymethyl fumarate) were dissolved in 30 ml of benzene and the resulting solution was refluxed for 20 minutes through a Dean-Stark apparatus.

After cooling the solution at 50° to 60° C., 0.7 g of 4β-vinylthio-[1,2-diacetoxymethyl]-azetidin-2-one dissolved in 10 ml of benzene were added and the resulting solution was refluxed for 2 hours. The title compound was obtained in almost quantitative yield and can be used as a crude mixture for the next step. A pure sample was obtained by preparative TLC for analytical purposes.
PMR (CDCl₃):
2.07δ (s, 3CH₃CO),
2.97δ (dd, Jgem 18 Hz, Jvic trans=2 Hz, C—3—Hβ),
3.40δ (dd, Jgem—18 Hz, Jvic cis=4 Hz, c—3—Hα),
4.70δ (d, Jvic=6 Hz,

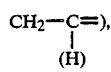

4.77δ (s,

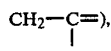

5.0–5.4δ (m, C—4—H and

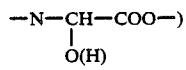

5.77δ (s, —COO—CH₂—OCO),
6.12δ (t, Jvic=6 Hz,

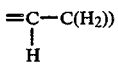

EXAMPLE 10

4β-Vinylthio-[1,2-diacetoxymethyl]-1-[-acetoxymethyloxycarbonyl-1-chloromethyl]-azetidin-2-one Reaction (7)-(8)

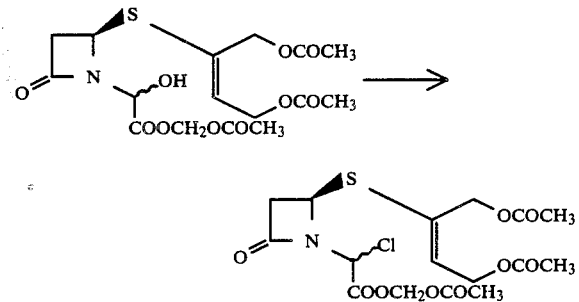

0.6 g of 4β-vinylthio[1,2-diacetoxymethyl]-1-[acetoxymethyloxycarbonyl-1-hydroxymethyl]-azetidin-2-one dissolved in 15 ml of tetrahydrofuran were cooled at 0° C.; 0.115 ml of pyridine and 0.104 ml of thionyl chloride were added and the resulting mixture was stirred for 10 minutes. The insoluble material was filtered off and the solution was evaporated "in vacuo" at room temperature to give the title compound in high yield. A sample was purified on preparative TLC for analytical purposes, but the crude mixture can be used without purification for the next step.
PMR (CDCl₃):
2.14δ (s, 3 CH₃CO),
3.10δ (dd, Jgem=15.5 Hz, Jvic trans=2 Hz, C—3—Hβ),
3.55δ (d, Jgem=15.5 Hz, Jvic cis=5 Hz, C—3—Hα),
4.77δ (d, Jvic=6.5 Hz,

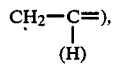

4.83δ (s, CH₂—C=),
5.4–5.9δ (m, C—4—H and —N—CHCl—COO—),
5.88δ (s, —COO—CH₂—OCO—),
6.13δ (t, Jvic=6.5 Hz,

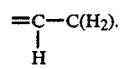

EXAMPLE 11

4β-Vinylthio-[1,2-diacetoxymethyl]-1-[acetoxymethyloxycarbonyl-1-triphenylphosphoranylidenemethyl]-azetidin-2-one Reaction (8)–(9)

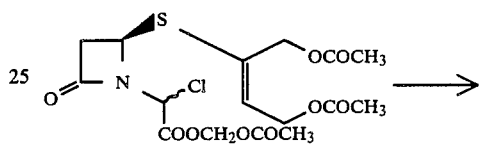

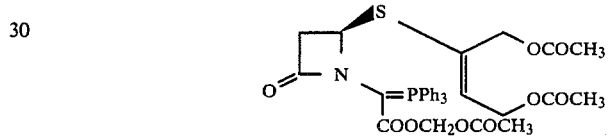

A solution of 0.430 g of 4β-vinylthio-[1,2-diacetoxymethyl]-1-[1-acetoxymethyloxycarbonyl-1-chloromethyl]-azetidin-2-one in 5 ml of tetrahydrofuran and 5 ml of dioxane containing 0.520 g of triphenylphosphine and 0.08 ml of pyridine, was stirred overnight at 50° C. The resulting phosphorane was purified by column chromatography on silica gel eluting with 70:30 dichloromethaneethylacetate; 0.400 g of the title compound were obtained.
PMR (CDCl₃):
2.05δ (s, 3 CH₃CO),
4.70δ (d Jvic=6.5 Hz,

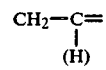

4.73δ

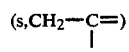

5.77δ (s, —COO—CH₂—OCO—)
5.90δ (t, Jvic—6.5 Hz,

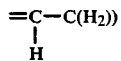

7.1–8.0δ (m, 3C₆H₅).

EXAMPLE 12

4β-Acetylglycolylthio-1-[1-acetoxymethyloxycarbonyl-1-triphenylphosphoranylidenemethyl]-azetidin-2-one Reaction (10)–(11)

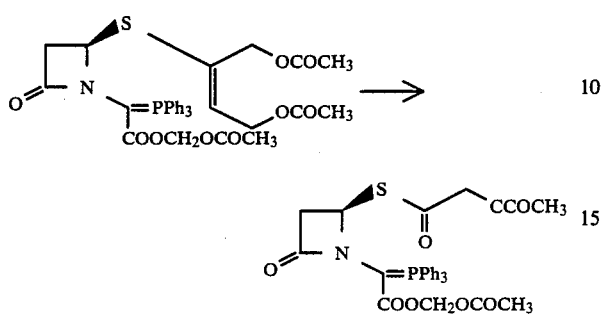

0.7 g of 4β-vinylthio-[1,2-diacetoxymethyl]-1-[1-acetoxymethyloxy-carbonyl-1-triphenylphosphoranylidenemethyl]-azetidin-2-one were dissolved in 40 ml of dichloromethane and, after cooling at −20° C., 50 ml of a 10% solution of trifluoroacetic acid in dichloromethane were added. After a few minutes, a flow of ozone in oxygen was bubbled into the solution at −20° C. until a slightly blue color appeared. At this point, the reaction was stopped and a few drops of trimethylphosphite were added. The organic solution was washed with a saturated solution of $NaHCO_3$ and dried over $Na_2SO_4$ to give 0.550 of the title compound.

PMR ($CDCl_2$):
  2.10 and 2.15δ (two d, 2 $CH_3CO$),
  4.72δ (s, —CO—$CH_2$—OCO—),
  5.64δ (s, —COO—$CH_2$—OCO),
  7.1–8.0δ (m, 3 $C_6H_5$).

EXAMPLE 13

(5R)-Acetoxymethyl-2-acetoxymethyl-2-penem-3-carboxylate Reaction (11)–(1)

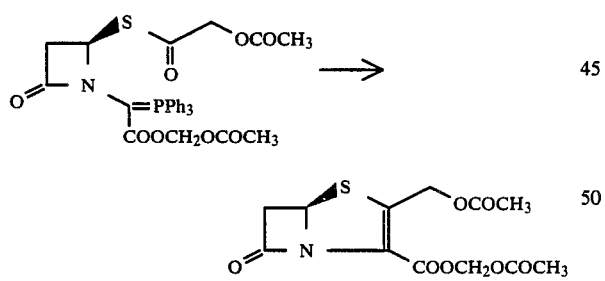

0.7 g of 4β-acetylglycolythio-1-[1-acetoxymethyloxycarbonyl-1-triphenylphosphoranylidenemethyl]-azetidin-2-one were dissolved in 30 ml of dry toluene and heated at refluxing temperature for 2 hours. The reaction mixture, consisting of the title compound and triphenylphosphine oxide, was purified by a short column chromatography on silica gel, eluting with 97:3 dichloromethaneethylacetate, to give 0.250 g of acetoxymethyl-2-acetoxymethyl-2-acetoxymethyl-2-penum-3-carboxylate.

PMR ($CDCl_3$):
  2.11 and 2.13δ (two s, 2 $CH_3CO$),
  3.49δ (dd, Jgem=16.5 Hz, Jvic trans=2 Hz, C—6—Hβ),
  3.85δ (dd, Jgem=16.5 Hz, Jvic cis=3.8 Hz, C—6—Hα),
  5.12 and 5.45δ (two d, Jgem=15.5 Hz, =C—$CH_2$),
  5.68δ (dd, Jvic=3.8 and 2 Hz, C—5—H),
  5.87δ (s, —COO—$CH_2$—OCO—).

IR ($CHCl_3$):
  1800 cm$^{-1}$ β-lactam C=O
  1750–1725 cm$^{-1}$ esters C=O

U.V. (EtOH):
  λmax 325 nm.

MS:
  m/e 315.04108 (M+) calculated for $C_{12}H_{13}NO_7S$ 315.04127.

EXAMPLE 14

4β-Vinylthio-(1,2-diacetoxymethyl)-1-(1-p.nitrobenzyloxycarbonyl-1-hydroxymethyl)-azetidin-2-one Reaction (6)–(7)

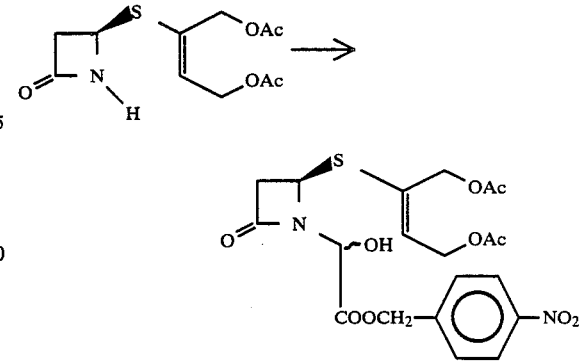

The title compound was obtained following the same procedure of Example 9, using p-nitrobenzylglyoxylate which had been freshly prepared by the ozonolysis of p-nitrobenzylfumarate. Quantitative yield.

PMR ($CDCl_3$) δ:
  2.1 (s, 6H); 2.8–3.7 (m, 2H); 4.7–4.9 (m, 5H);
  5.1–5.6 (m, 2H); 5.2 (m, 1H); 6.1 (m, 1H);
  7.5–8.3 (m, 4H).

EXAMPLE 15

4β-Vinylthio-(1,2-diacetoxymethyl)-(1-p-nitrobenzyloxycarbonyl-1-chloromethyl)-azetidin-2-one Reaction (7)–(8)

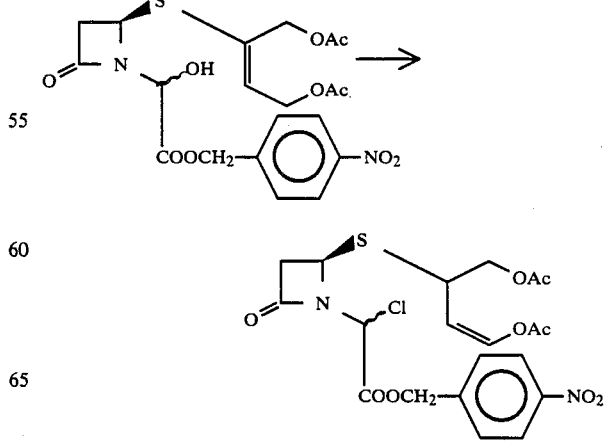

The title compound was obtained following the procedure shown in Example 10.

PMR (CDCl₃) δ:
2.1 (s, 6H); 2.8–3.7 (m, 2H); 4.7–4.9 M, 4H);
5.2–5.4 (m, 1H0; 5.4 (m, 2H); 6.1–6.3 (m, 2H);
7.5–8.4 (m, 4H).

EXAMPLE 16

4β-Vinylthio-(1,2-diacetoxymethyl)-1-(1-p-nitrobenzyloxycarbonyl-1-triphenylphosphoranylidenemethyl)-azetidin-2-one Reaction (8)–(9)

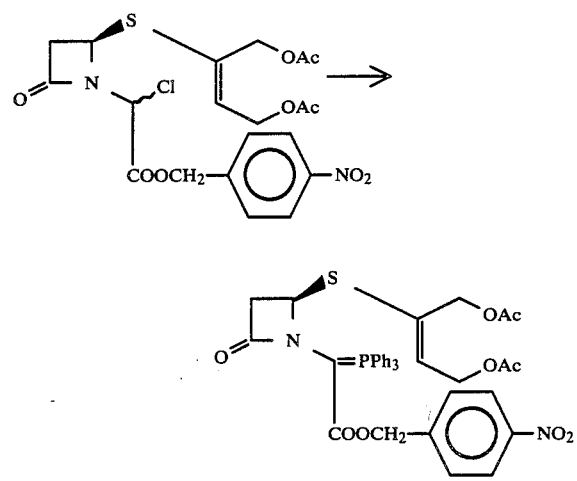

The title compound was obtained following the procedure of Example 11.

EXAMPLE 17

4β-Acetylglycolylthio-1-(1-p-nitrobenzyloxycarbonyl-1-triphenylphosphoranylidenemethyl)-azetidin-2-one Reaction (9)–(11)

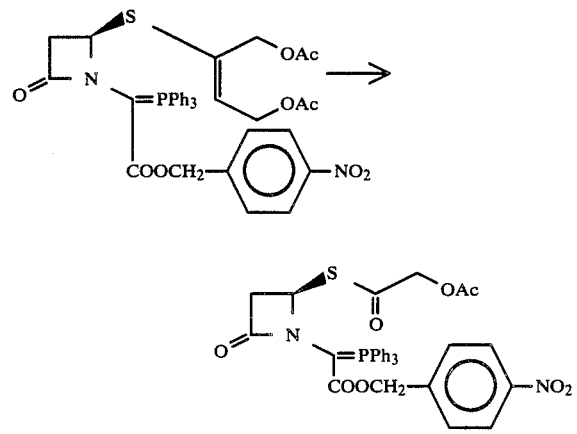

The title compound was obtained following the procedure of Example 12.

EXAMPLE 18

(5R)-p-nitrobenzyl-2-acetoxymethyl-2-penem-3-carboxylate Reaction (11)-(1)

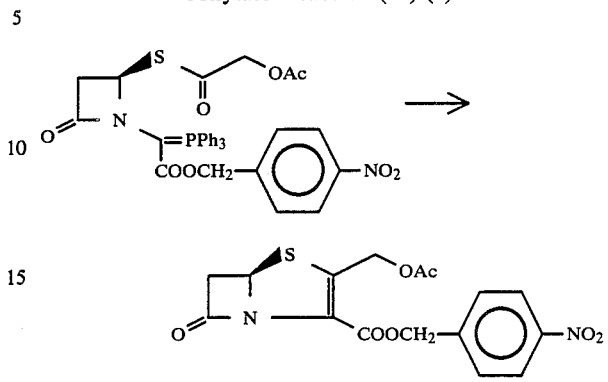

The title compound was obtained following the procedure of Example 13.

PMR (CDCl₃):
3.75 (1H, dd, J=2.3 Hz, 16.8 Hz, H—6α)
3.87 (1H, dd, J=3.6 Hz, 16.8 Hz, H—6β)
5.14 (1H, d, J=15.8, —C—CH₂O—);
5.50 (1H, dd, J=15.8 Hz, =C—CH₂O);
5.71 (1H, dd, J=2.3 Hz, 3.6 Hz, H—5).
$[\alpha]_D + 87°$ (C 1.2 CHCl₃).

IR (CHCl₃):
1800 (β-lactam, 1750 and 1720 cm⁻¹).

UV (EtOH):
265 (ε 11000) and 322 (7000) nm.

M.S.:
m/e 378 (M⁺).

M.p.:
122°–123° C.

EXAMPLE 19

(5R)-2-Acetoxymethyl-2-penem-3-carboxylic acid Reaction (1)

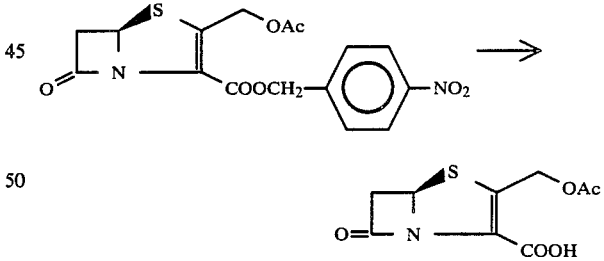

200 mg of (5R)-p-nitrobenzyl-2-acetoxymethyl-2-penem-3-carboxylate prepared as described in Example 18, were dissolved in 12 ml of ethyl acetate. Then 8 ml of a 0.2M NaHCO₃ solution and 400 mg of 10% Pd/C were added and the resulting biphasic mixture was shaken under hydrogen for 60 minutes. After filtering the catalyst, the aqueous phase was acidified with 20 ml of 5% aqueous citric acid and extracted three times with methylene chloride. The organic layers were dried over Na₂SO₄ and evaporated to give 60 mg of the title compound.

I.R. (CHCl₃):
1790 (β lactam), 1735 and 1700 cm⁻¹.

U.V. (EtOH):

EXAMPLE 20

4β-(1-Hydroxymethyl)-vinylthio-1-[1-methoxycarbonyl-2-methyl-2-propenyl]-azetidin-2-one-S-oxide Reaction (2)–(3)

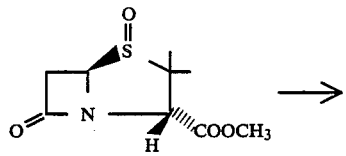 →

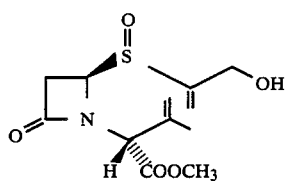

4 g of penicillanic acid methyl ester S-oxide were dissolved in 15 ml of toluene and refluxed with 15 ml of propargyl alcohol for 8 hours. After evaporating in vacuo, the residue was purified by short column chromatography on silica gel, eluting with dichloromethane-ethyl acetate 1:1. 2.8 g of the title compound were obtained.
PMR (CDCl$_3$) δ:
1.96 (bs, 3H,

);

2.91 and 3.35 (dd, 2H, J=2 Hz, 5 Hz, 15 Hz, CO—CH$_2$—CH—S); 3.78 (s, 3H, COOCH$_3$; 4.36 (bs, 2H, CH$_2$OH);
4.90–5.25 (m, 3H, CH—COOCH$_3$

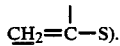);

5.35 (m, 1H, CH$_2$—CH—S);
5.88 (s, 2H,

CH$_2$=C—S).

EXAMPLE 21

4β-1-(Hydroxymethyl)-vinylthio-1-[1-methoxycarbonyl-2-methyl-1-propenyl]-azetidin-2-one-S-oxide Reaction (3)–(4)

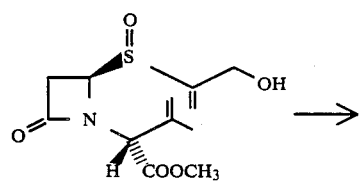 →

-continued

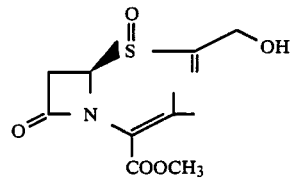

3.0 g of 4β-(1-hydroxymethyl)-vinylthio-1-[1-methoxycarbonyl-2-methyl-2-propenyl]-azetidin-2-one-S-oxide were dissolved in 100 ml of dichloromethane and left at room temperature for a few hours. After evaporating the solvent, the residue consisted of pure title compound in a quantitative yield.
PMR (CDCl$_3$) δ:
2.08 (s, 3H,

);

2.18 (s, 3H,

);

2.7–3.6 (m, J=2 Hz, 5 Hz, 16 Hz, CO—CH$_2$—CH—S);
3.78 (s, 3H, COOCH$_3$); 4.35 (s, 2H, CH$_2$OH);
5.32 (m, 1H, CH—S); 5.90 (bs, 2H, =CH$_2$).

EXAMPLE 22

4β-(1-Bromomethyl)-vinylthio-1-[1-methoxycarbonyl-2-methyl-1-propenyl]-azetidin-2-one Reaction (4)–(12)

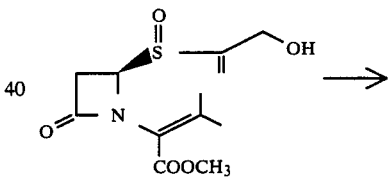 →

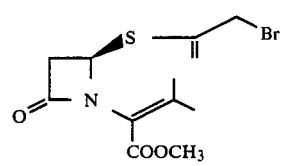

1.8 g of 4β-(1-hydroxymethyl)vinylthio-1-[1-methoxycarbonyl-2-methyl-1-propenyl]-azetidin-2-one-S-oxide were dissolved in 40 ml of dimethylformamide and cooled at −20° C. Thereafter, 0.7 ml of pyridine and 3.0 ml of PBr$_3$ were added and the mixture left for 15 minutes while stirring. Ethyl acetate was added and the organic layr was shaken with a NaHCO$_3$ saturated solution, washed with water, and then dried over Na$_2$SO$_4$ giving, after evaporation of the solvent, 1.6 g of the title compound.
PMR (CDCl$_3$) δ:
2.04 (s, 3H,

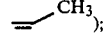);

2.24 (s, 3H,

3.24 (dd, J=2.8, 5, 16 Hz, 2H,

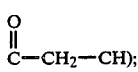

3.75 (s, 3H, OCH₃); 4.02 (s, 2H, CH₂Br);
5.24 (bs, 1H, =CH); 5.37 (dd, J=2.8 Hz, 5 Hz, 1H, CH₂—CH—S); 5.60 (bs, 1H, =CH).

EXAMPLE 23

4β-[1-(1-Methyl-1-H-tetrazol-5-yl)-thiomethyl]-vinylthio-1-[1-methoxycarbonyl-2-methyl-1-propenyl]-azetidin-2-one Reaction (12)

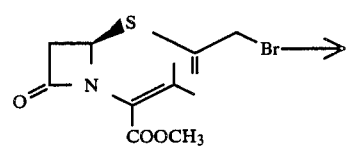

1.4 g of 4β-(1-bromomethyl)-vinylthio-1-[1-methoxycarbonyl-2-methyl-1-propenyl]-azetidin-2-one were dissolved in 25 ml of tetrahydrofuran and cooled at 0° C. Then 0.8 g of 1-methyl-5-thiol-tetrazol sodium salt were added to the solution and the mixture was stirred for three hours at room temperature. After filtering the insolubles, the mixture was diluted with ethyl acetate, washed with water, dried over Na₂SO₄ and evaporated. The residue consisted of 2.0 g of pure title compound.
PMR (CDCl₃) δ:
2.00 (s, 3H,

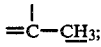

2.22 (s, 3H,

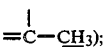

2.70–3.80 (m, 2H, J=2 Hz, 5 Hz, CO—CH₂—CH—S);
3.72 (s, 3H, COOCH₃); 3.95 (s, 3H, N—CH₃);
4.10 (s, 2H, CH₂—S); 5.18 (bs, 1H,

5.36 (m, 1H, CH₂—CH—S); 5.57 (bs, 1H,

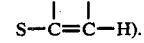

EXAMPLE 24

4β-(1-Methyl-1-H-tetrazol-5-yl)thioacetylthio-1-methoxy-oxaloylazetidin-2-one Reaction (12)–(13)

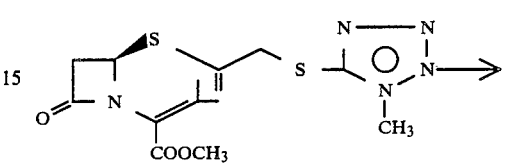

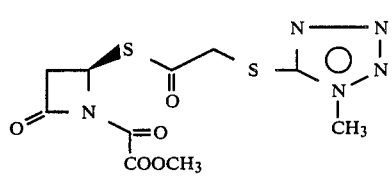

1.8 g of 4β-[1-(1-methyl-1-H-tetrazol-5-yl)-thiomethyl]-vinylthio-1-[1-methoxycarbonyl-2-methyl-1-propenyl]-azetidin-2-one were dissolved in 200 ml of dichloromethane and cooled at −78° C. A flow of oxonized oxygen was bubbled through the solution until a blue color appeared. A few drops of P(OCH₃)₃ were added and the mixture was raised to room temperature and evaporated to give 1.3 g of the title compound.
PMR (CDCl₃) δ:
2.9–3.7 (m, 2H, COCH₂CH—S); 3.85 (s, 3H, COOCH₃); 3.98 (s, 3H, N—CH₃); 4.35 (s, 2H, CH₂S); 5.75 (m, 1H, CH₂CH—S).

EXAMPLE 25

4β-(1-Methyl-1-H-tetrazol-5-yl)-thioacetylthio-azetidin-2-one Reaction (13)–(14)

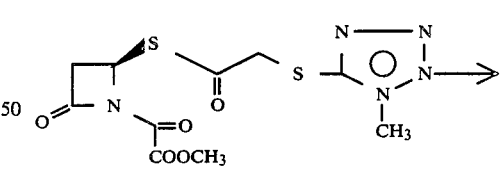

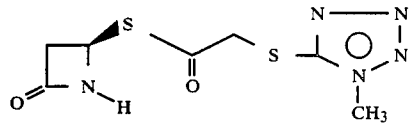

1.2 g of 4β-(1-methyl-1-H-tetrazol-5-yl)-thioacetylthio-1-methoxyoxaloyl-azetidin-2-one were dissolved in a 1:1 ethyl aceate-methanol mixture and a few grams of silica gel were added under vigorous stirring. After one hour, the insoluble material was filtered off and the solution evaporated in vacuo. The title compound was crystallized from methanol-ethyl ether in a quantity of 0.6 g.

EXAMPLE 26

4β-(a-Methyl-1-H-tetrazol-5-yl)-thioacetylthio-1-(1-acetoxymethyloxycarbonyl-1-hydroxymethyl)-azetidin-2-one Reaction (14)–(15)

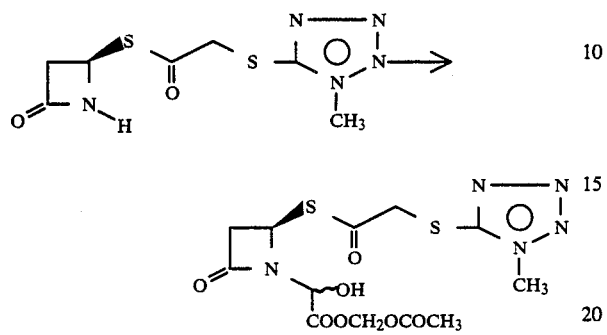

1.5 g of 4β-(1-methyl-1-H-tetrazol-5-yl)-thioacetylthioazetidin-2-one were refluxed in 50 ml of benzene with 1.2 g of acetoxymethylglyoxylate (freshly prepared by the ozonolysis of diacetoxymethylfumerate). The reaction was completed after 3 hours. The crude oil obtained after evaporating the solvent can be used for the next step without further purification. A sample was purified on TLC for spectroscopic data.

PMR (CDCl$_3$) δ:
2.05 (s, 3H); 2.7–3.8 (m, 2H); 3.95 (s, 3H);
4.30 (s, 2H); 5.40 (s, 1H); 5.50 (m, 1H);
5.80 (s, 2H).

EXAMPLE 27

4β-(1-Methyl-1-H-tetrazol-5-yl)-thioacetylthio-1-(1-acetoxymethyloxycarbonyl-1-chloromethyl)-azetidin-2-one Reaction (15)–(16)

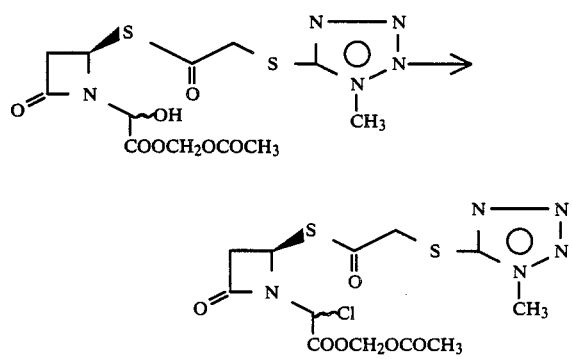

The oil obtained from Example 26 consisting of crude 4β-(1-methyl-1-H-tetrazol-5-yl)-thioacetylthio-1-(1-acetoxymethyloxycarbonyl-1-hydroxymethyl)-azetidin-2-one, was dissolved in anhydrous tetrahydrofuran (20 ml) and treated at 0° C. with equimolar amounts of pyridine and thionyl chloride until all starting material disappeared. After filtering the insoluble material, the filtrate was used immediately for the next step.

EXAMPLE 28

4β-1-Methyl-1-H-tetrazol-5-yl)-thioacetylthio-1-(1-acetoxymethyloxycarbonyl-1-triphenyl-phosphoranylidenemethyl)-azetidin-2-one Reaction (16)–(11)

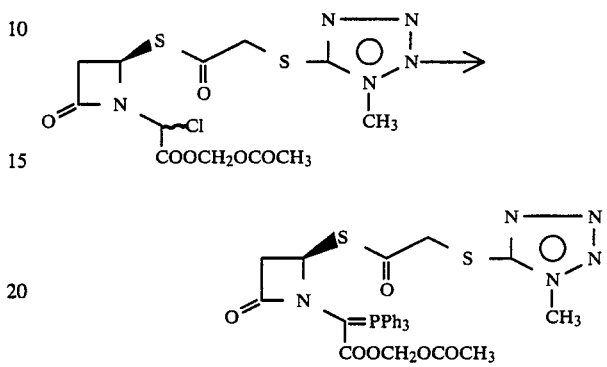

To a solution containing crude 4β-(1-methyl-1-H-tetrazol-5-yl)-thioacetylthio-1-(1-acetoxymethyloxycarbonyl-1-chloromethyl)-azetidin-2-one, 800 mg of triphenylphosphine and 0.4 ml of pyridine were added and the resulting mixture was heated at 60° to 70° C. for a few hours. The phosphorane produced by this reaction was purified on silica gel eluting with dichloromethaneethyl acetate (1:1).

EXAMPLE 29

(5R)-Acetoxymethyl-2-[(1-methyl-1-H-tetrazol-5-yl)-thiomethyl]-2-penem-3-carboxylate Reaction (11)–(1)

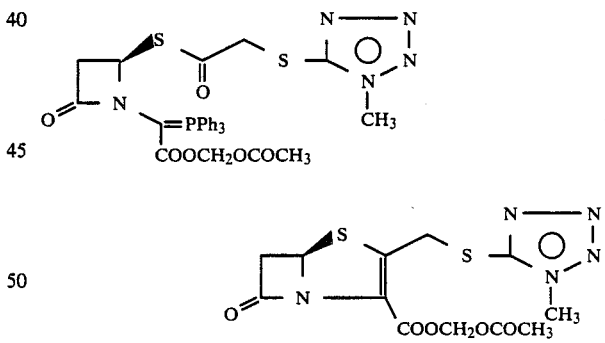

0.500 g of 4β-(1-methyl-1-H-tetrazol-5-yl)-thioacetylthio-1-(1-acetoxymethyloxycarbonyl-1-triphenyl-phosphoranylidenemethylazetidin-2-one were dissolved in 30 ml of toluene and heated at 100° C. for two hours. The title compound was purified from PPh$_3$O by short column chromatography on silica gel eluting with dichloromethane-ethyl acetate. (8:2)

PMR (CDCl$_3$) δ:
2.15 (s, 3H, COC$\underline{H}_3$); 3.30–4.03 (m, J=4 Hz, 2 Hz, —CH$_2$—(6); 3.97 (s, 3H, —NC$\underline{H}_3$);
4.56 (d, J=14 Hz, 1H, $\underline{H}$CH—S);
4.84 (d, J=14 Hz, 1H, HC$\underline{H}$—S), 5.65 (dd, J=4 Hz, 2 Hz, 1H, H—5α); 5.38 (s, 2H, COOC$\underline{H}_2$O).

EXAMPLE 30

(5R)-2-(1-Methyl-1-H-tetrazol-5-yl)-thiomethyl-2-penem-3-carboxylic acid Reaction (1)

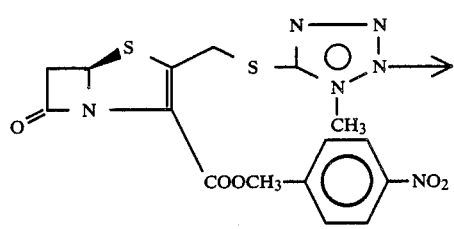

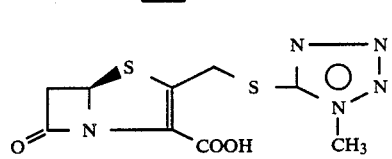

The title compound was obtained following the procedure set out in Example 19. The (5R) p-nitrobenzoyl-2-(1-methyl-1-H-tetrazol-5-yl)-thiomethyl-2-penem-3-carboxylate was obtained by a process similar to the process described in the previous examples. I.R. (CHCl$_3$): 1800 ($\beta$ lactam), 1750 and 1720.

EXAMPLE 31

Methyl-6$\alpha$-(1'-hydroxyethyl)-penicillinate-S-oxide Reaction (17)–(2)

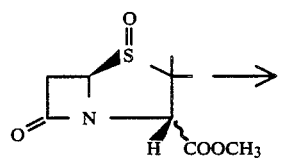

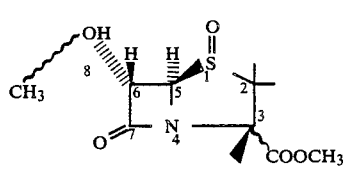

A solution of methylpenicillinate S-oxide (2.3 g) in 50 ml of anhydrous tetrahydrofuran was cooled at −78° C. Lithium diisopropylamide (freshly prepared from 5 ml of diisopropylamine and 20 ml of a 1.6M BuLi hexane solution) dissolved in anhydrous tetrahydrofuran was added and the mixture left at −78° C. for 10 minutes. 5 ml of acetaldehyde were successively added and the solution was stirred for 15 minutes. The reaction was then quenched with a NH$_4$Cl saturated aqueous solution, extracted with ethyl acetate, washed twice with water, and dried over Na$_2$SO$_4$. After evaporation of the solvent, the residue was shortly purified by column chromatography on silica gel eluting with dichloromethane-ethyl acetate (1:1). The title compound was obtained in a quantity of 1.5 g. The title compound consisted of a 2:3 mixture of epimers at the hydroxyl bearing carbon based on the PMR, being the new C$_6$–C$_8$ bond only in the $\alpha$-position because of the stereospecificity of the reaction due to the conditions employed. PMR (CDCl$_3$) $\delta$:

1.27 (s, 3H, $\alpha$—CH$_3$); 1.40 (d, 3H, J=5.7 Hz, CH$_3$—CHOH) major isomer; 1.48 (d, 3H, J=5.7 Hz, CH$_3$—CHOH) minor isomer; 1.70 (s, 3H, —CH$_3$); 3.4–3.8 (m, LH, H—6); 3.80 (s, 3H, COOCH$_3$); 4.1–4.7 (m, 1H, CHOH); 4.50 (s, 1H, H—3); 4.98 (d, J=1.9 Hz, 1H, H—5) minor isomer; 5.05 (d, J=1.9 Hz, H—5) major isomer.

EXAMPLE 32

Methyl-6-[1-hydroxyethyl]-3-penicillanate Reaction (17)–(2)

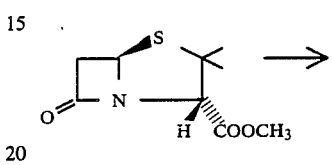

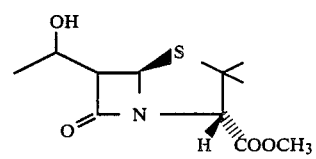

To a solution of 2.2 g of methylpenicillanate in 30 ml of anhydrous tetrahydrofuran, a slight excess of lithium diisopropylamide was added at −78° C. under nitrogen. An excess of acetaldehyde was added, the mixture stirred for 5 minutes, quenched with trace acetic acid, poured into water, and extracted with methylene chloride. The organic layers after being dried over Na$_2$SO$_4$ and evaporated "in vacuo" gave 0.8 g of the title compound.

EXAMPLE 33

Methyl-6-[1-p-nitrobenzyloxycarbonyloxyethyl]-3-penicillanate Reaction (2)

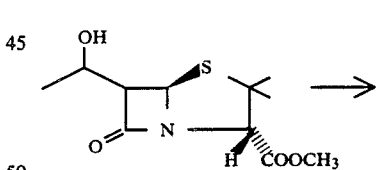

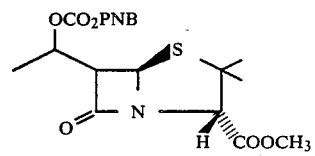

1.2 g of methyl-6-[1-hydroxyethyl]-3-penicillanate were dissolved in 40 ml of tetrahydrofuran, cooled at −78° C., and treated with one equivalent of butyl lithium. 1.2 equivalents of p-nitrobenzyloxycarbonylchloride were added to the previous mixture; after 30 minutes at −78° C., the reaction was left at room temperature for 60 minutes, poured into water, and extracted with methylene chloride: 1.4 g of the title compound were obtained after drying over Na$_2$SO$_4$ and evaporating.

EXAMPLE 34

Methyl-6-[1-p-nitrobenzyloxycarbonyloxyethyl]-3-penicillanate-S-oxide Reaction (17)–(2)

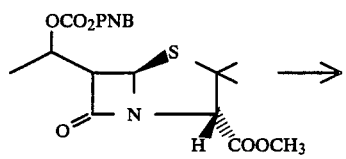

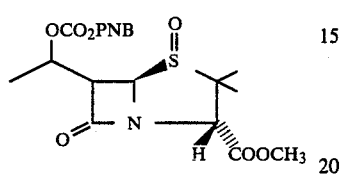

1.8 g of methyl-6-[1-p-nitrobenzyloxycarbonyloxyethyl]-3-penicillanate were dissolved in 50 ml of methylene chloride and treated at 0° C. with 1.5 equivalents of m-chloroperbenzoic acid. The organic phase was shaken with a NaHCO$_3$ saturated solution, extracted, dried over Na$_2$SO$_4$, and evaporated giving 1.4 g of the sulphoxide set out in the title.

The following data have been ascertained for the compound of the example in both the erithro and threo configurations depending upon the starting material. Similar data appear herein for the compounds of Examples 35, 36, 44, 46, 96, 97, and 98.

Erithro

PMR (CDCl$_3$):
- 1.20 (s, 3H, αCH$_3$)
- 1.55 (d, J=6.5 Hz, 3H, CH$_3$CH)
- 1.70 (s, 3H, βCH$_3$)
- 3.82 (s, 3H, COOCH$_3$)
- 3.88 (dd, J=2.0, 4.0 Hz, 1H, H—6)
- 4.50 (s, 1H, H—3)
- 4.85 (d, J=2.0 Hz, 1H, H—5)
- 5.19 (m, 1H, CHO)
- 5.31 (s, 2H, CH$_2$Ph)
- 7.4–8.4 (m, 4H, PhNO$_2$.

Threo

PMR (CDCl$_3$):
- 1.23 (s, 3H, α—CH$_3$)
- 1.51 (d, J=6.5 Hz, 3H, CH$_3$CH)
- 1.70 (s, 3H, β—CH$_3$)
- 3.77 (dd, J=2.0, 7.0 Hz, 1H, H—6)
- 3.81 (s, 3H, COOCH$_3$)
- 4.51 (s, 1H, H—3)
- 4.96 (d, J=2.0 Hz, 1H, H—5)
- 5.28 (m, 1H, CHO)
- 5.32 (s, 2H, CH$_2$Ph)
- 7.4–8.4 (m, 4H, PhNO$_2$).

EXAMPLE 35

4β-Vinylthio-[1,2-diacetoxymethyl]-3-[1-p-nitrobenzyloxycarbonyloxyethyl]-1-methoxycarbonyl-2-methyl-2-propenyl]-azetidine-2-one-S-oxide Reaction (2)–(3)

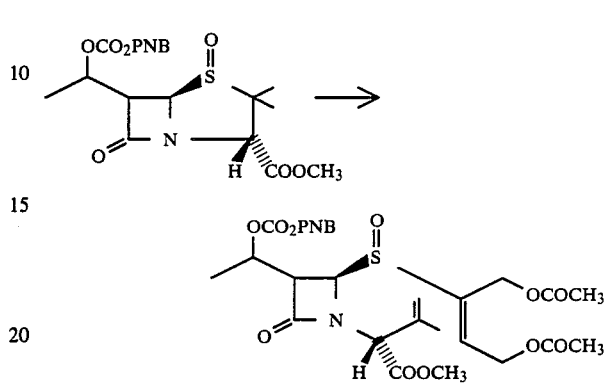

A solution of 2.0 g of methyl-6-[1-p-nitrobenzyloxycarbonyloxyethyl]-3-penicillanate-S-oxide and 2.4 g of butyndiol diacetate in 50 ml of toluene was refluxed for 24 hours. The trapped compound was then purified by silica gel column chormatography eluting with 9:1 dichloromethane-ethyl acetate. 1.1 g of the title compound were obtained.

Erithro

PMR (CDCl$_3$):
- 1.46 (d, J=6.0 Hz, 3H, CH$_3$CH)
- 2.06 (s, 9H, OCOCH$_3$, OCOCH$_3$,

- 3.72 (s, 3H, COOCH$_3$)
- 3.73 (m, 1H, H—6)
- 4.80 (d, J=6.0 Hz, 2H,

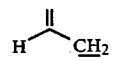

- 4.87 (s, 2H, CH$_2$OAc)
- 5.00 (s, 2H, =CH$_2$)
- 5.26 (s, 2H, COCH$_2$Ph)
- 4.9–5.2 (m, 3H, CHOH, H—5, CHCOOCH$_3$)
- 6.42 (t, J=6.0 Hz, 1H,

- 7.4–8.4 (m, 4H, PhNO$_2$).

IR(CHCl$_3$)
- 1750 cm$^{-1}$ C=O esters,
- 1780 cm$^{-1}$ C=O β-lactam.

Threo

PMR(CDCl$_3$):
- 1.40 (d, J=6.0 Hz, 3H, CH$_3$CH)
- 1.97, 2.05, 2.10 (s, 9H, OCOCH$_3$, OCOCH$_3$,

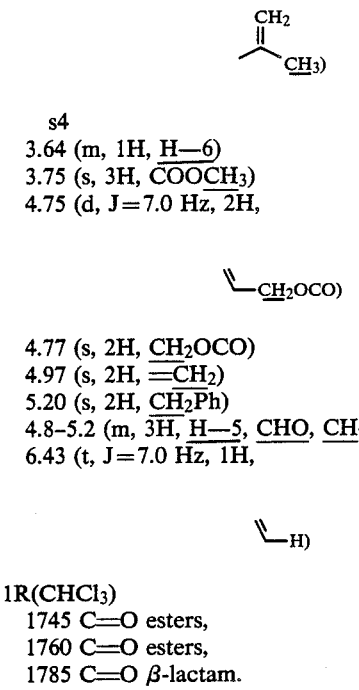

s4
3.64 (m, 1H, H—6)
3.75 (s, 3H, COOCH₃)
4.75 (d, J=7.0 Hz, 2H,

—CH₂OCO)

4.77 (s, 2H, CH₂OCO)
4.97 (s, 2H, =CH₂)
5.20 (s, 2H, CH₂Ph)
4.8–5.2 (m, 3H, H—5, CHO, CH—COOCH₃)
6.43 (t, J=7.0 Hz, 1H,

—H)

IR(CHCl₃)
1745 C=O esters,
1760 C=O esters,
1785 C=O β-lactam.

EXAMPLE 36

4β-Vinylthio-[1,2-diacetoxymethyl]-3-[1-p-nitrobenzyloxycarbonyloxyethyl]-1-[methoxycarbonyl-2-methyl-1-propenyl]-azetidin-2-one-S-oxide Reaction (3)–(4)

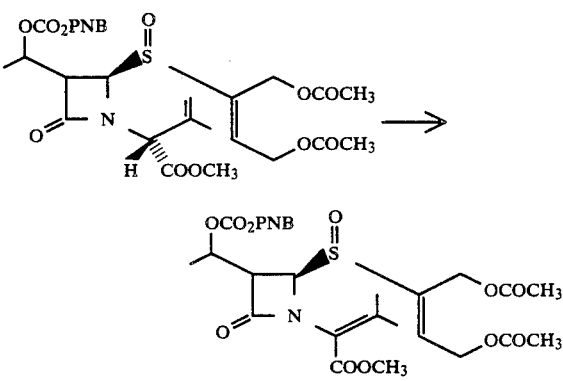

1.3 g of 4β-vinylthio-[1,2-diacetoxymethyl]-3-[1-p-nitrobenzyloxycarbonyloxyethyl]-1-[methoxycarbonyl-2-methyl-2-propenyl]-azetidin-2-one-S-oxide were dissolved in 80 ml of dichloromethane; 0.3 ml of triethylamine was added and the mixture was left at room temperature for 2 hours. The pure title compound was quantitatively obtained upon evaporation of the solvent.

Erithro

PMR (CDCl₃):
1.50 (d, J=6.5 Hz, 3H, CH₃CH)
2.05, 2.07 (s, 9H,

OCOCH₃, OCOCH₃)
2.27 (s, 3H,

=CH₃)

3.73 (s, 3H, COOCH₃)
3.80 (m, 1H, H—6)
4.78 (d, J=6.0 Hz, 2H,

H—CH₂)

4.83 (s, 2H, CH₂OCO)
4.9–5.3 (m, 2H, H—5, CHOH)
5.25 (s, 2H, CH₂Ph)
6.42 (t, J=6.0 Hz, 1H,

H—)

7.4–8.4 (m, 4H, PhNO₂).

IR (CHCl₃)
1710 cm⁻¹ C=O unsaturated esters
1755 cm⁻¹ C=O esters
1775 cm⁻¹ C=O β-lactam.

Threo

PMR (CDCl₃):
1.45 (d, J=6.0 Hz, 3H, CH₃CH)
2.10 (s, 9H, OCOCH₃, OCOCH₃,

=CH₃)

2.28 (s, 3H,

=CH₃)

3.70 (dd, J=2.0, 6.0 Hz, 1H, H—6)
3.77 (s, 3H, COOCH₃)
4.82 (d, J=7.0 Hz, 2H,

CH₂OCO)

4.82 (s, 2H, CH₂OCO)
5.10 (d, J=2.0 Hz, 1H, H—5)
5.0–5.3 (m, 1H, CHO)
5.23 (s, 2H, CH₂Ph)
6.52 (t, J=7.0 Hz, 1H,

H—)

7.4–8.4 (m, 4H, PhNO₂).
IR (CHCl₃)
1710 cm⁻¹ C=O unsaturated ester,
1755 cm⁻¹ C=O esters,
1780 cm⁻¹ C=O β-lactam.

EXAMPLE 37

4β-Vinylthio-[1,2-diacetoxymethyl]-3-[1-p-nitrobenzyloxycarbonyloxyethyl]-1-methoxyoxaloyl-azetidin-2-one-S-oxide Reaction (4)–(5)

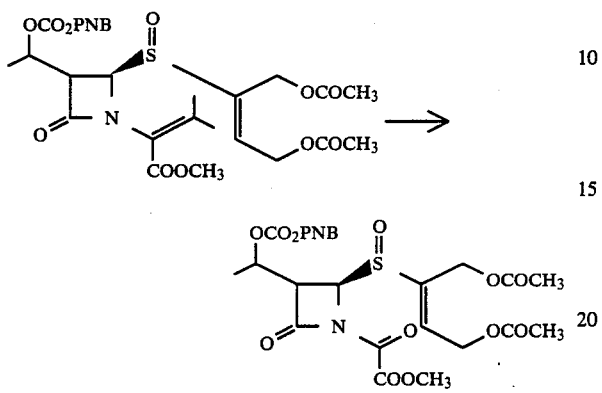

A solution of 1.1 g of 4β-vinylthio-[1,2-diacetoxymethyl]-3-[1p-nitrobenzyloxycarbonyloxyethyl]-1-[methoxycarbonyl-2-methyl-1-propenyl]-azetidin-2-one-S-oxide in 100 ml of dichloromethane was cooled at −78° C. Ozone in oxygen was bubbled into the solution until a blue color appeared. The solution was shaken with an aqueous solution of Na₂SO₂O₅ and dried over Na₂SO₄. 0.5 g of the title compound were obtained after evaporation.

EXAMPLE 38

4β-Vinylthio-[1,2-diacetoxymethyl]-3-[1p-nitrobenzyloxycarbonyloxyethyl]-1-methoxyoxaloyl-azetidin-2-one Reaction (5)

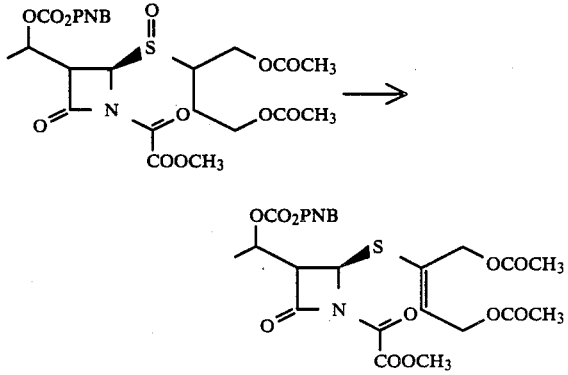

A solution of 0.8 g of 4β-vinylthio-[1,2-diacetoxymethyl]-3-[1-p-nitrobenzyloxycarbonyloxyethyl]-1-methoxyoxaloyl-azetidin-2-one in 15 ml of anhydrous dimethylformamide was cooled at −20° C. and 0.6 ml of phosphorous tribomide was added. The reaction was diluted with ethyl acetate after 10 minutes and washed twice with a solution of NaHCO₃. The organic phase, dried over Na₂SO₄ and evaporated, gave 0.4 g of the reduced compound.

EXAMPLE 39

4β-Vinylthio-[1,2-diacetoxymethyl]-3-[1-p-nitrobenzyloxycarbonyloxyethyl]-azetidin-2-one Reaction (5)–(6)

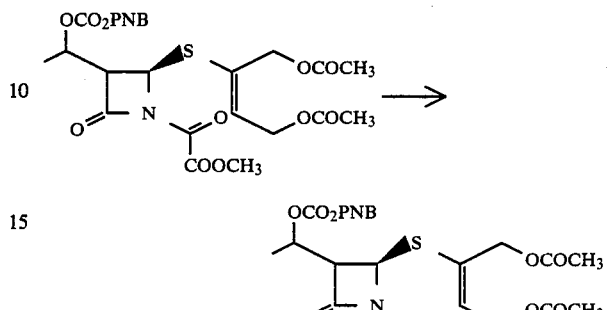

1.2 g of 4β-vinylthio-[1,2-diacetoxymethyl]-3-[1-p-nitrobenzyloxycarbonyloxyethyl]-1-methoxyoxaloyl-azetidin-2-one were dissolved in methanol and 2 g of silica gel were added to the solution. After 60 minutes the insoluble material was filtered and the organic phase evaporated. Short column chromatography resulted in 0.4 g of the title compound.

EXAMPLE 40

4β-Vinylthio-[1,2-diacetoxymethyl]-3-[1-p-nitrobenzyloxycarbonyloxyethyl]-1-[1-acetoxymethyloxycarbonyl-1-hydroxymethyl]-azetidin-2-one Reaction (6)–(7)

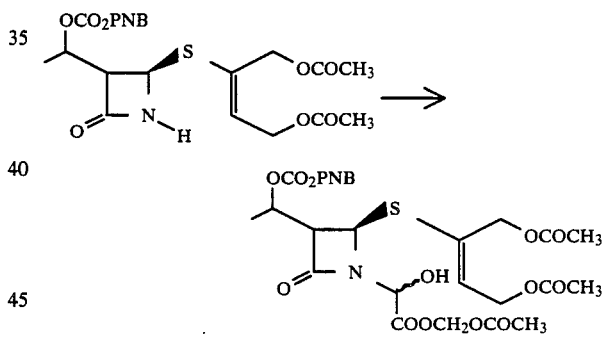

0.6 g of 4β-vinylthio-[1,2-diacetoxymethyl]-b 3-[1-p-nitrobenzyloxy-carbonyloxyethyl]-azetidin-2-one, dissolved in 30 ml of benzene, and 0.6 g of acetoxymethyl fumarate (freshly prepared from the ozonolysis of diacetoxymethyl fumarate) were refluxed. The reaction was completed after two hours. The condensation product can be used for the next step without further purification.

EXAMPLE 41

4β-Vinylthio-[1,2-diacetoxymethyl]-3-[1-p-nitrobenzyloxycarbonyloxyethyl]-1-[1-acetoxymethyloxycarbonyl-1-chloromethyl]-azetidin-2-one Reaction (7)–(8)

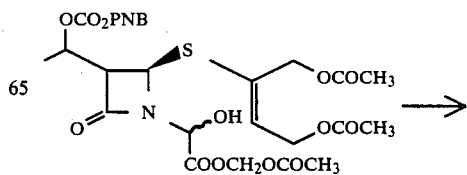

-continued

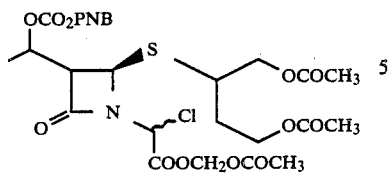

0.5 g of 4β-vinylthio-[1,2-diacetoxymethyl)-3-[1-p-nitrobenzyloxycarbonyloxyethyl]-1-[1-acetoxymethyloxycarbonyl-1-hydroxymethyl]-azetidin-2-one were dissolved in 12 ml of anhydrous tetrahydrofuran and cooled at 0° C.; thereafter 1.1 equivalents of pyridine and 1.1 equivalents of thionyl chloride were added to the solution. The mixture was stirred for 10 minutes. The insoluble material was filtered off and the solution evaporated at room temperature to give the title compound in nearly quantitative yields. The product can be used without further purfication for the next step.

EXAMPLE 42

4β-Vinylthio-[1,2-diacetoxymethyl]-3-[1-p-nitrobenzyloxycarbonyloxyethyl]-1-[acetoxymethyloxycarbonyl-1-triphenylphosphoranylidenemethyl]-azetidin-2-one Reaction (8)–(9)

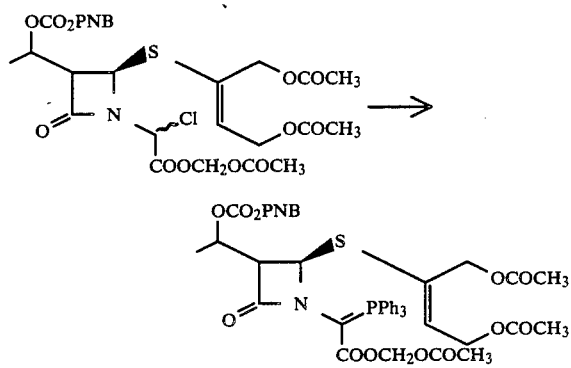

A solution of 0.760 g of 4β-vinylthio-[1,2-diacetoxymethyl]-3-[1-p-nitrobenzoyloxycarbonyloxyethyl]-1-[1-acetoxymethyloxycarbonyl-1-hydroxymethyl]-azetidin-2-one in 10 ml of tetrahydrofuran and 10 ml of dioxane, with 2 equivalents of triphenylphosphine and 1.1 equivalents of pyridine, was stirred overnight at +50° C. The phosphorane was purified by silica gel column chromatography, eluting with 79:30 dichloromethane-ethyl acetate. 0.480 g of the title compound were obtained.

EXAMPLE 43

4β-Acetylglycolylthio-3-[1-p-nitrobenzyloxycarbonyloxyethyl]-1-[1-acetoxymethyloxycarbonyl-1-triphenylphosphoranylidenemethyl]-azetidin-2-one (Reaction (9)–(11)

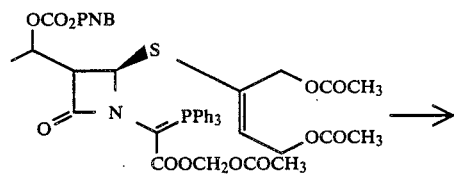

-continued

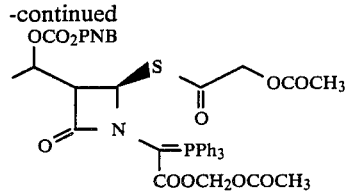

0.45 g of 4β-vinylthio-[1,2-diacetoxymethyl]-3-[1-p-nitrobenzyloxycarbonyloxyethyl]-1-[acetoxymethyloxycarbonyl-1-triphenylphosphoranylidenemethyl]-azetidin-2-one were dissolved in 50 ml of dichlormethane and cooled at −20° C.; then 30 ml of trifluoroacetic acid solution in dichloromethane were added. After a few minutes ozone in oxygen was bubbled into the solution until a slightly blue color appeared. The reaction was stopped and a few drops of trimethylphosphite were added. The organic phase was washed with a saturated solution of NaHCO$_3$ and dried over Na$_2$SO$_4$ to give 0.26 g of the title compound.

EXAMPLE 44

4β-Vinylthio-[1,2-diacetoxymethyl]-3-[1-p-nitrobenzyloxycarbonyloxyethyl]-1-[methoxycarbonyl-2-methyl-1-propenyl]-azetidin-2-one Reaction (4)–(12)

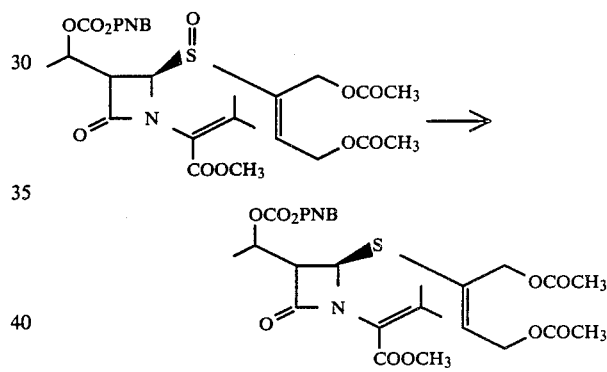

1.5 g of vinylthio-[1,2-diacetoxymethyl]-3-[1-p-nitrobenzyloxycarbonyloxyethyl]-1-[methoxycarbonyl-2-methyl-1-propenyl]-azetidin-2-one S-oxide were dissolved in 10 ml of anhydrous dimethylformamide and cooled at −20° C.; 0.8 ml of phosphorous tribromide were added. The mixture was stirred for 10 hours, diluted with ethyl acetate, and washed twice with a NaHCO$_3$ saturated solution. The organic layer, when dried over Na$_2$SO$_4$ and evaporated gave 1.1 g of the title compound.

Erithro

PMR (CDCl$_3$): 1.53 (d, J=6.5 Hz, 3H, C$\underline{H}$$_3$CH)
2.05 (s, 9H, OCOC$\underline{H}$$_3$, OCOC$\underline{H}$$_3$,

=⟨CH$_3$)

2.22 (s, 3H,

=⟨CH$_3$)

3.42 (dd, J=2.0, 4.0 Hz, 1H, H—6)
3.72 (s, 3H, COOC$\underline{H}$$_3$)
4.63 (d, J=6 Hz, 2H

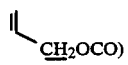

4.72 (s, 2H, C<u>H</u>₂OCO)
5.0–5.6 (m, 2<u>H</u>, <u>H</u>—5, C<u>H</u>O)
5.30 (s, 2H, C<u>H</u>₂Ph)
5.95 (t, J=6 Hz, 1H,

7.5–8.4 (m, 4H, P<u>h</u>NO₂).
IR (CHCl₃)
   1725 cm⁻¹ C=O unsaturated ester
   1750 cm⁻¹ C=O ester
   1725 cm⁻¹ C=O β-lactam.

Threo

PMR (CDCl₃):
   1.53 (d, J=6.0 Hz, 3H, C<u>H</u>₃CH)
   2.02, 2.03 (s, 9H, OCOC<u>H</u>₃, OCOC<u>H</u>₃,

2.23 (s, 3H,

3.30 (dd, J=2.0, 7.0 Hz, 1H, <u>H—6</u>)
3.73 (s, 3H, COOC<u>H</u>₃)
4.60 (d, J=7.0 Hz, 2H,

4.70 (s, 2H, C<u>H</u>₂OCO)
5.1–5.3 (m, 1<u>H</u>, C<u>H</u>O)
5.27 (s, 2H, C<u>H</u>₂Ph)
5.38 (d, J=2.0 Hz, 1H, <u>H—5</u>)
5.96 (t, J=7.0 Hz, 1H,

7.3–8.3 (m, 4H, P<u>h</u>NO₂)
IR (CHCl₃)
   1725 cm⁻¹ C=O unsaturated ester;
   1755 cm⁻¹ C=O esters;
   1770 cm⁻¹ C=O β-lactam.

EXAMPLE 45

4β-Acetylglycolythio-3-[1-p-nitrobenzyloxycarbonyloxyethyl]-1-methoxyoxalyl-azetidin-2-one Reaction (12)–(13)

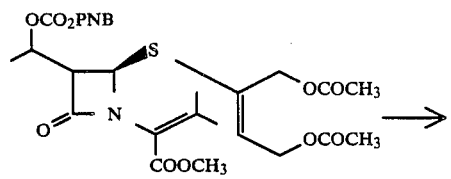

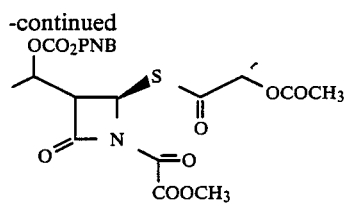

1.4 g of 4β-vinylthio-[1,2-diacetoxymethyl]-3-[1-p-nitrobenzyloxycarbonyloxyethyl]-1-[methoxycarbonyl-2-methyl-1-propenyl]-azetidin-2-one in 120 ml of dichloromethane were cooled to −78° C. Then ozone oxygen was bubbled through the solution until a blue color appeared. The solution was shaken with an aqueous solution of Na₂S₂O₅ and dried over Na₂SO₄. Evaporation of the solution gave 0.8 g of the title compound.

EXAMPLE 46

4β-Acetylglycolythio-3-[1-p-nitrobenzyloxycarbonyloxyethyl]-azetidin-2-one Reaction (13)–(14)

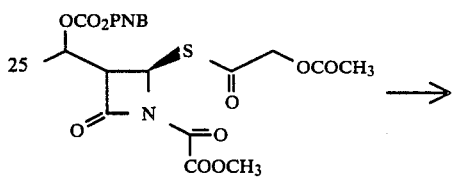

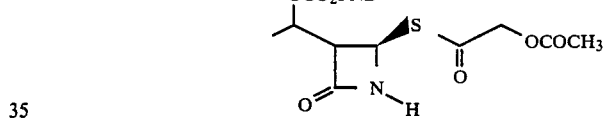

0.800 g of 4β-acetylglycolylthio-3-[1-p-nitrobenzyloxycarbonyloxyethyl]-1-methoxyoxalyl-azetidin-2-one were dissolved in 50 ml of methanol and a few grams of silica gel added. The mixture was left at room temperature for 60 minutes. The insoluble material was filtered off and the filtrate, after evaporation, gave 0.30 g of the title compound.

Erithro

PMR (CDCl₃):
   1.48 (d, J=6.0 Hz, 3H, C<u>H</u>₃ CH);
   2.18 (s, 3H, OCOC<u>H</u>₃);
   3.44 (dd, J=2.0, 5.0 Hz, 1H, <u>H—6</u>);
   4.73 (s, 2H, C<u>H</u>₂OCO);
   5.0–5.3 (m, 1<u>H</u>, C<u>H</u>O);
   5.15 (d, J=2.0 Hz, <u>H—5</u>);
   5.27 (s, 2H, C<u>H</u>₂Ph);
   6.58 (bs, 1H, N<u>H</u>);
   7.4–8.4 (m, 4<u>H</u>, P<u>h</u>NO₂).
IR (CHCl₂)
   1705 cm⁻¹ S—C=O;
   1775 cm⁻¹ C=O ester;
   1795 cm⁻¹ C=O β-lactam;
   3400 cm⁻¹ NH.

Threo

PMR (CDCl₃):
   1.43 (d, J=6.0 Hz, 3H, C<u>H</u>₃CH);
   2.17 (s, 3H, OCOC<u>H</u>₃);
   3.39 (dd, J=2.0, 7.0 Hz, 1H, <u>H—6</u>);
   4.72 (s, 2H, C<u>H</u>₂OCO);
   5.2–5.4 (m, 1<u>H</u>, C<u>H</u>O);

5.24 (s, 2H, C$\underline{H_2}$Ph);
5.32 (d, J=2.0 Hz, 1H, $\underline{H\text{—}5}$);
6.80 (bs, 1H, N$\underline{H}$);
7.4–8.4 (m, 4$\underline{H}$, $\underline{Ph}$NO$_2$).
IR (CHCl$_3$)
1705 cm$^{-1}$

1760 cm$^{-1}$ C=O ester;
1785 cm$^{-1}$ C=O β-lactam;
3400 cm$^{-1}$ NH.

EXAMPLE 47

4β-Acetylglycolylthio-3-[1-p-nitrobenzyloxycarbonyloxyethyl]-1-[1-acetoxymethyloxycarbonyl-1-hydroxymethyl]-azetidin-2-one Reaction (14)–(15)

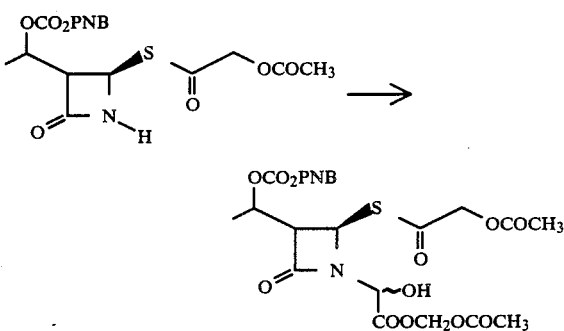

0.5 g of 4β-acetylglycolythio-3-[1-p-nitrobenzyloxycarbonyloxyethyl]-1-[1-acetoxymethyloxycarbonyl-1-hydroxymethyl]-azetidin-2-one and 0.5 g of acetoxymethyl fumarate in 30 ml of benzene were refluxed until the reaction was completed (two hours). The obtained title compound can be used for the next step without further purification.

EXAMPLE 48

4β-Acetylglycolthio-3-[1-p-nitrobenzyloxycarbonyloxyethyl]-1-[1-acetoxymethyloxycarbonyl-1-chloromethyl]-azetidin-2-one Reaction (15)–(16)

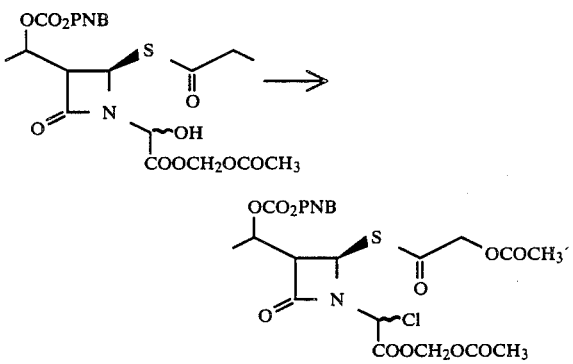

0.35 g of 4β-acetylglycolylthio-3-[1-O-nitrobenzyloxycarbonyloxyethyl]-1-[1-acetoxymethyloxycarbonyl-1-hydroxymethyl]-azetidin-2-one were dissolved in 10 ml of anhydrous tetrahydrofuran at 0° C. Then 1.1 equivalents of pyridine and 1.1 equivalents of thionyl chloride were added and the mixture was stirred for 10 minutes. The precipitate was filtered and the filtrate, after evaporation, gave the title compound in quantitative yield. The crude product was used as such for the next step.

EXAMPLE 49

4β-Acetylglycolylthio-3-[1-p-nitrobenzyloxycarbonyloxyethyl]-1-[1-acetoxymethyloxycarbonyl-1-triphenylphosphoranylidenemethyl]-azetidin-2-one Reaction (16)–(11)

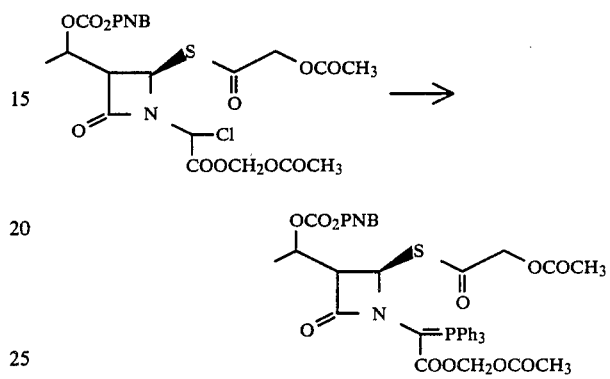

0.400 g of 4β-acetylglycolylthio-3-[1-p-nitrobenzyloxycarbonyloxy-ethyl]-1-[1-acetoxymethyloxycarbonyl-1-chloromethyl]-azetidin-2one were dissolved in 20 ml of a 1:1 mixture of tetrahydrofuran and dioxane. Thereafter 2 equivalents of triphenylphosphine and 1.1 equivalents of pyridine were added and the mixture stirred overnight at 50° C. The title compound was purified by silica gel column chromatography, eluting with 70-30 dichloromethane-ethyl-acetate. 0.280 g of the titled phosphorane were obtained.

EXAMPLE 50

(5R)-Acetoxymethyl-6-[1-p-nitrobenzyloxycarbonyloxyethyl]-2-acetoxymethyl-2-penem-3-carboxylate Reaction (11)–(1)

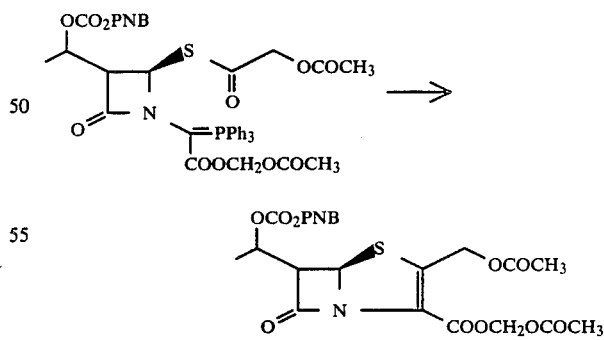

0.210 g of 4β-acetylglycolylthio-3-[1-p-nitrobenzyloxycarbonyloxyethyl]-1-[1-acetoxymethyloxycarbonyl-1-triphenylphosphoranylidenemethyl]-azetidin-2-one were dissolved in 7 ml of toluene and the solution was refluxed for two hours. Purification by short column chromatography when eluting with 95:5 dichloromethane-ethyl acetate, gave 0.05 g of the title compound.

EXAMPLE 51

(5R)-Acetoxymethyl-6-[1-hydroxyethyl]-2-acetoxymethyl-2-penem-3-carboxylate Reaction (1)

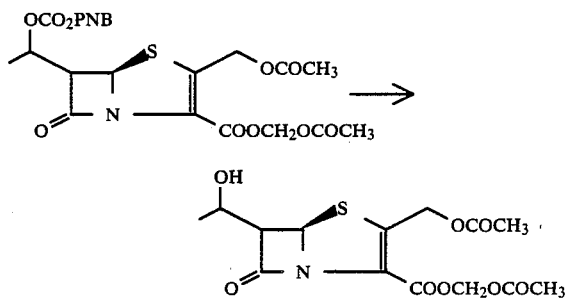

0.060 g of (5R)-acetoxymethyl-6-[1-nitrobenzyloxycarbonyloxyethyl]-2-acetoxymethyl-2-penem-3-carboxylate were poured in a water-ethanol-$K_2HPO_4$ mixture and hydrogenolyzed with 10% Pd/C. A quick purification by silica gel column chromatography gave 0.015 g of the title compound.

Operating as described in the previous working examples, but employing 5-methyl-2-thiol-1,3,4-thiadiazole; 5-thiol-1,2,3-triazole; or thiolpyrazine instead of 1-methyl-5-thiol-tetrazole, (5R)-2-[5'-methyl-1',3',4'-thiadiazol-2'-yl)-thiomethyl]-2-penem-3-carboxylic acid; (5R)-2-[1',2',3'-triazol-5yl)-thiomethyl]-2-penem-3-carboxylic acid; (5R)-2-(pyrazinyl)-thiomethyl-2-penem-3-carboxylic acid; (5R)-6-[1'-hydroxyethyl]-2-[5''-methyl-1'',3'',4''-thiadiazol-2''-yl)thiomethyl]-2-penem-3-carboxylic acid; (5R)-6-[1'-hydroxyethyl]-2-[1'',2'',3''-triazol-5''-yl)thiomethyl]-2-penem-3-carboxylic acid; and (5R)-6-[1'-hydroxyethyl]-2-(pyrazinyl)thiomethyl-2-penem-3-carboxylic acid respectively were prepared.

Operating as previously described, but reducing the methyl-6-[1'-hydroxyethyl]-3-penicillinate following the widely-known procedure, the corresponding 6-ethyl-derivatives were obtained.

EXAMPLE 52

6α-Methoxypenicillanic-acid-trichloroethylester-S-oxide Reaction (17)–(2)

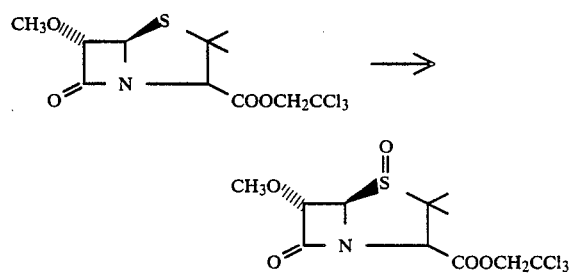

800 mg of 6α-methoxypenicillanic-acid-trichloroethylester (prepared according to Giddings et al, Tetrahedron Letters, 11, 995 (1978) were dissolved in 20 ml of dichloromethane and treated portionwise with 570 mg of m-chloroperbenzoic acid at room temperature. The organic phase was washed with a $NaHCO_3$-saturated solution and evaporated. The title compound crystallized from ethyl ether. Obtained 650 mg. M.p. 120°–121° C.

PMR ($CDCl_3$)δ:
1.35 (s, 3H, α—$\underline{CH_3}$); 1,75 (s, 3H, β—$\underline{CH_3}$);
3.58 (s, 3H, O$\underline{CH_3}$;
4.52 (s, 1H, 3—$\underline{H}$);
4.70–5.00 (two d, 2H, J=9 Hz, $\underline{CH_2}OCl_3$);
4.87 (d, 1H, J=1.5 Hz, $\underline{H}$—5);
5.07 (d, 1H, J=1.5 Hz, $\underline{H}$—6).

EXAMPLE 53

3α-Methoxy-4β-vinylthio-[1,2-diacetoxymethyl]-1-[trichloroethoxycarbonyl-2-methyl-2-propenyl]-azetidin-2-one-S-oxide Reaction (2)–(3)

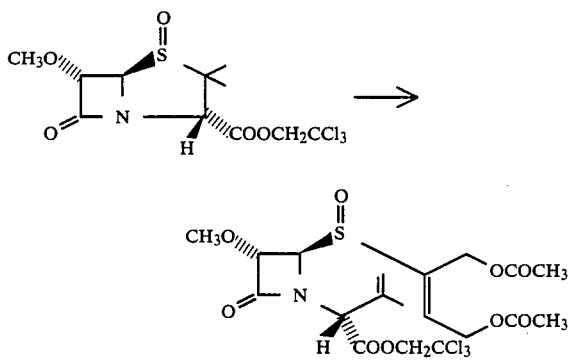

550 g of 6α-methoxypenicillanic acid-trichloroethylester-S-oxide were dissolved in 25 ml of toluene; 1.2 g of butyndiol diacetate were added and the resulting solution was refluxed for 10 hrs. The reaction mixture was purified by silica gel column chromatography eluting with 10% ethyl acetate-dichloromethane. 450 mg of the title compound were obtained.

PMR ($CDCl_3$)δ:
2.01 (bs, 3H, 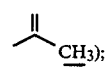

2.08–2.10 (two s, 6H, O$CO\underline{CH_3}$; 3.45 (s, 3H, O$CH_3$);
4.75–5.00 (multiplet, 8H); 5.18 (bs, 2H, =$\underline{CH_2}$); 5.27 (d, 1H, J=1.5 Hz, H—3); 6.57 (t, 1H, J=6.0 Hz, 

EXAMPLE 54

3α-Methoxy-4β-vinylthio-[1,2-diacetoxymethyl]-1-[1-trichloroethoxycarbonyl-2-methyl-1-propenyl]-azetidin-2-one-S-oxide Reaction (3)–(4)

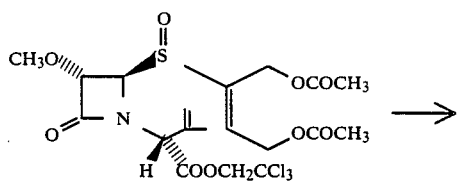

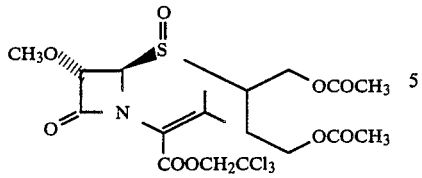

400 mg of 3α-methoxy-4β-vinylthio-[1,2-diacetoxymethyl]-1-[trichloroethoxycarbonyl-2-methyl-2-propenyl]-azetidin-2-one-S-oxide were dissolved in 10 ml of dichloromethane and stirred at room temperature with a few drops of triethylamine for 2 hrs. Evaporating the solvent gave the pure title compound.
PMR (CDCl$_3$)δ:
2.10 (s, 6H,

OCOC$\underline{H}$$_3$); 2.14 (s, 3H, OCOC$\underline{H}$$_3$);
2.40 (s, 3$\overline{H}$,

), 3.49 (s, 3H, OC$\underline{H}$$_3$);
4,82–4.88 (two s, 4$\overline{H}$,

OCOCH$_3$, C$\underline{H}$$_2$CCl$_3$);
4.91 (d, 2H, J=6.0 Hz,

;

4.95 (d, 1H,
J=2.0 Hz, H—4); 5.23 (d, 1H, J=2.0 Hz, H—3);
6.60 (t, 1H, J=6.0 Hz,

.

EXAMPLE 55

3α-Methoxy-4β-vinylthio-[1,2-diacetoxymethyl]-1-[trichloroethoxyoxaloyl-azetidin-2-one-S-oxide Reaction (4)–(5)

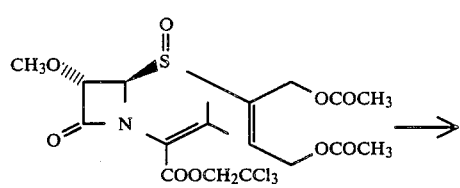

2 g of 3α-methoxy-4β-vinylthio-[1,2-diacetoxymethyl]-1-[1-trichloroethoxycarbonyl-2-methyl-1-propenyl]-azetidin-2-one-S-oxide were dissolved in 200 ml of dichloromethane and cooled to −70° C. Ozone in oxygen was passed through the solution until a blue color appeared. A few drops of trimethylphosphite were added. Evaporating the solvent gave the pure title compound.
PMR (CDCl$_3$)δ:
2.10–2.12 (two s, 6H, OCOC$\underline{H}$$_3$);
3.58 (s, 3H, OC$\underline{H}$$_3$);
4.75–5.05 (m, 6$\overline{H}$, C$\underline{H}$$_2$CCl$_3$,

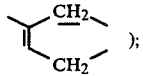);

5.07 (d, 1H, J=3.0 Hz, H—4);
5.22 (d, 1H, J=3.0 Hz, H—3);
6.61 (t, 1H, J=6.0 Hz,

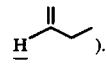.

EXAMPLE 56

3α-Methoxy-4β-vinylthio-[1,2-diacetoxymethyl]-1-trichloroethoxyoxaloyl-azetidin-2-one Reaction (5)

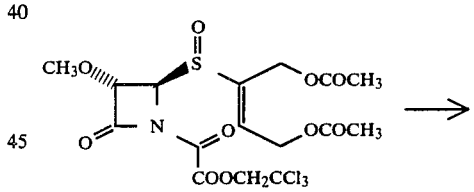

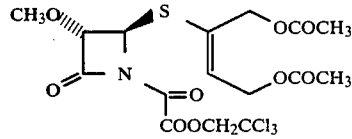

800 mg of 3α-methoxy-4β-vinylthio-[1,2-diacetoxymethyl]-1-trichloroethoxyoxaloyl-azetidin-2-one-S-oxide were dissolved in 30 ml of anhydrous dimethylformamide and cooled to −20° C. 0.5 ml of PBr$_3$ were and the mixture was stirred for 10 minutes. The reaction mixture was poured into ethyl acetate and washed several times with water: the residue, after drying over Na$_2$SO$_4$, consisted essentially of the title compound and was used for the next step without further purification.
PMR (CDCl$_3$)δ:
2.08–2.11 (two s, 6H, OCOC$\underline{H}$$_3$);
3.61 (s, 3H, OC$\underline{H}$$_3$);
4.5–5.0 (m, 7$\overline{H}$);
5.38 (d, 1H, J=3.0 Hz, $\underline{H}$—3);

6.28 (t, 1H, J=6.5 Hz,

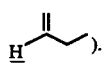).

EXAMPLE 57

3α-Methoxy-4β-vinylthio-[1,2-diacetoxymethyl]-azetidin-2-one Reaction (5)–(6)

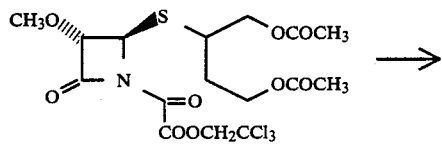

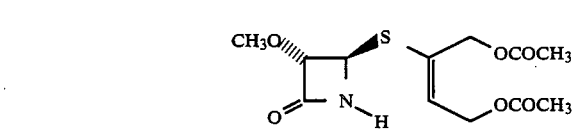

The crude residue obtained from the previous Example 56 was dissolved in 100 ml of methanol and 3 g of silica gel were added under stirring. The mixture was stirred for two hours; after filtering SiO2, the residue was purified by silica gel column chromatography eluting with 20% ethyl acetate-dichloromethane. There was obtained 400 mg of the title compound.
PMR (CDCl3)δ:
  2.08–2.11 (two s, 6H, OCOCH3);
  3.55 (s, 3H, OCH3);
  4.68 (d, J=6.5 Hz, 2H

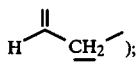);

4.81 (bs, 3H,

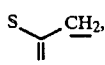

H—4);
4.86 (d, J=2.0 Hz, 1H, H—3);
6.04 (t, J=6.5 Hz, 1H,

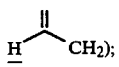

6.50 (bs, 1H, NH).

EXAMPLE 58

3α-Methoxy-4β-vinylthio-[1,2-diacetoxymethyl]-1-[1-acetoxymethyloxycarbonyl-1-hydroxymethyl]-azetidin-2-one Reaction (6)–(7)

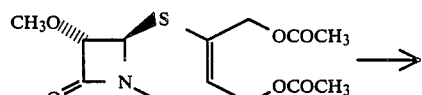

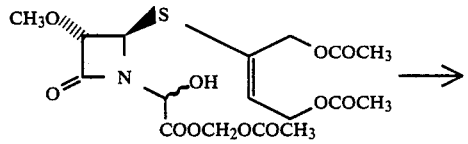

250 mg of 3α-methoxy-4β-vinylthio-[1,2-diacetoxymethyl]-azetidin-2-one were dissolved in 20 ml of benzene and refluxed for 3 hrs. with 300 mg of acetoxymethylglyoxylate (freshly prepared by ozonolysis of diacetoxymethylfumarate). The crude mixture was purified by silica gel column chromatography eluting with 40% ethyl acetate-dichloromethane to give 150 mg of pure title compound as a mixture of diastereoisomers.

EXAMPLE 59

3α-Methoxy-4β-vinylthio-[1,2-diacetoxymethyl]-1-[1-acetoxymethyloxycarbonyl-1-chloromethyl]-azetidin-2-one Reaction (7)–(8)

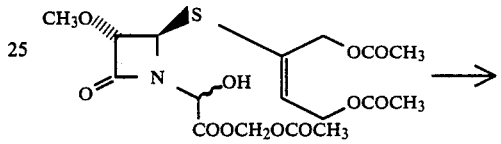

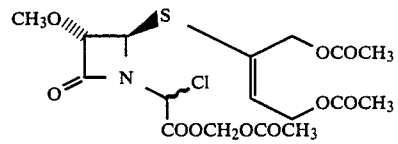

150 mg of 3α-methoxy-4β-vinylthio-[1,2-diacetoxymethyl]-1-[1-acetoxymethyloxycarbonyl-1-hydroxymethyl]-azetidin-2-one were dissolved in 10 ml of anhydrous tetrahydrofuran and cooled to −20° C.; stoichiometric amounts of pyridine and thionyl chloride were added and the mixture stirred for 10 minutes. The mixture was filtered from the insoluble material on celite and evaporated at room temperature to give a residue which was used for the next step without further purification.

EXAMPLE 60

3α-Methoxy-4β-vinylthio-[1,2-diacetoxymethyl]-1-[1-acetoxymethyloxycarbonyl-1-triphenylphosphoranylidenemethyl]-azetidin-2-one Reaction (8)–(9)

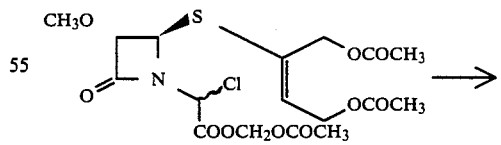

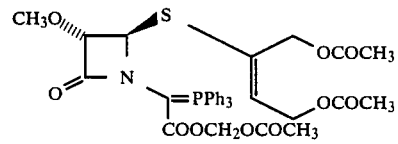

The crude residue obtained from Example 59, consisting of nearly pure 3α-methoxy-4β-vinylthio-[1,2-diacetoxymethyl]-1-[1-acetoxymethyloxycarbonyl-1- chloromethyl]-azetidin-2-one, was dissolved in 10 ml of toluene. 200 mg of triphenylphosphine were added and the resulting solution was refluxed under nitrogen for 2 hrs. The phosphorane was purified by short silica gel column chromatography, eluting with 40% ethyl acetate-dichloromethane, to give 180 mg of the title compound.

EXAMPLE 61

3α-Methoxy-4β-acetylglycolythio-1-[1-acetoxymethyloxycarbonyl-1-triphenylphosphoranylidenemethyl]-azetidin-2-one Reaction (9)–(11)

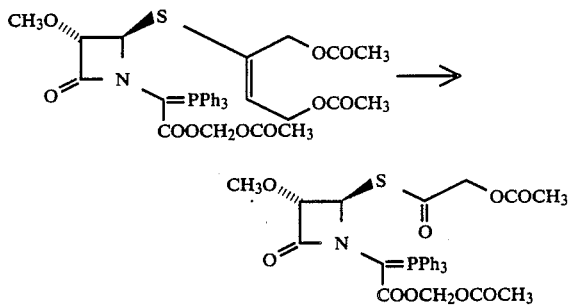

230 mg of 3α-methoxy-4β-vinylthio-[1,2-diacetoxymethyl]-1-[1-acetoxymethyloxycarbonyl-1-triphenylphosphoranylidenemethyl]-azetidin-2-one were dissolved in 50 ml of dichloromethane and, after cooling to −20° C., 0.5 ml of trifluoroacetic acid were added. Ozone in oxygen was bubbled through the solution until a blue color appeared. A few drops of trimethylphosphite were added and the reaction mixture was diluted with dichloromethane and washed several times with a NaHCO₃ saturated solution. After drying over Na₂SO₄ and evaporating the solvent, the residue (180 mg) consisted of pure title compound.

EXAMPLE 62

(5R)-Acetoxymethyl-6α-methoxy-2-acetoxymethyl-2-penem-3-carboxylate Reaction (11)–(1)

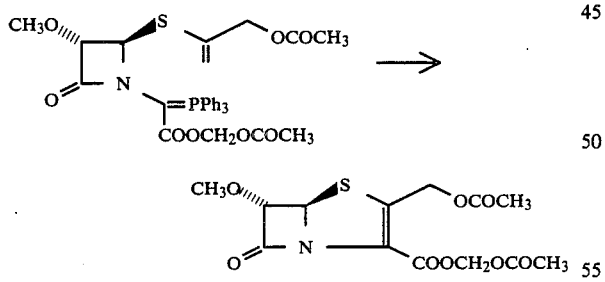

180 mg of 3α-methoxy-4β-acetylglycolythio-1-[1-acetoxymethyloxycarbonyl-1-triphenylphosphoranylidenemethyl]-azetidin-2-one were dissolved in 20 ml of toluene and refluxed under nitrogen for 2 hrs. The title compound was purified by silica gel column chromatography by eluting with 5% ethyl acetate-dichloromethane. There was obtained 50 mg of the compound.

PMR (CDCl₃) δ:
2.11 (s, 6H, OCOC$\underline{H}$₃), 3.56 (s, 3H, OC$\underline{H}$₃);
4.94 (d, J=1.7 Hz, 1H, H—4); 5.26 (center of dd, 2H,

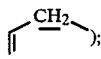

5.55 (d, J=1.7 Hz, 1H, H—3);
5.86 (s, 2H, COOC$\underline{H}$₂OCOCH₃).
IR (CHCl₃)
1795 (β lactam), 1745–1720 (esters).

EXAMPLE 63

(5R)-Acetonyl-6α-methoxy-2-acetoxymethyl-2-penem-3-carboxylate Reaction (6)–(7)–(8)–(9)–(11)–(1)

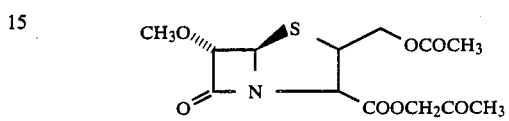

Operating as shown in Examples 58, 59, 60, 61, and 62 but using acetonyl glyoxylate in place of acetoxymethyl glyoxylate in Example 58, the title compound was obtained. IR 1800, 1745, 1710. (CHCl₃)

EXAMPLE 64

(5R)-6α-methoxy-2-acetoxymethyl-2-penem-3-carboxylic acid Reaction (1)

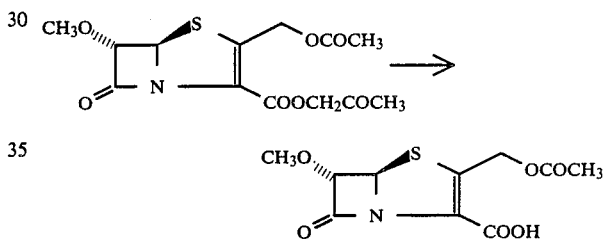

260 mg of (5R)-acetonyl-6α-methoxy-2-acetoxymethyl-2-penem-3-carboxylate were dissolved in 25 ml of tetrahydrofuran; the resulting solution was diluted with 5 ml of water and cooled to 0° C. 7.9 ml of a 0.1N NaOH aqueous solution were added and the mixture left at 0° C. for 10 minutes. The solution was washed twice with methylene chloride; the aqueous phase was poured under stirring with methylene chloride and 4 ml of a 20% citric acid aqueous solution were added. The aqueous phase was extracted twice with methylene chloride and the combined organic phases were dried over Na₂SO₄ and evaporated to give 80 mg of the title compound.
IR 1795, 1740, 1700. (CHCl₃).

EXAMPLE 65

4β-(1-Hydroxymethyl)-vinylthio-3α-(1-p-nitrobenzyloxycarbonyloxyethyl)-1-(1-methoxycarbonyl-2-methyl-2-propenyl)-azetidin-2-one-S-oxide. Reaction (2)–(3)

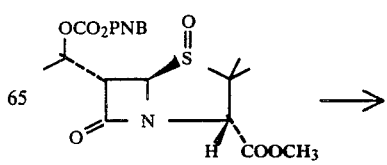

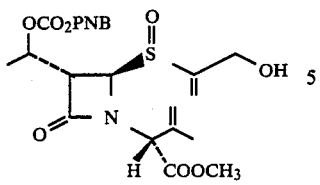

A solution of 2.6 g of methyl-6-(1-p-nitrobenzyloxycarbonyloxyethyl)-3-penicillinate-S-oxide and 8 ml of propargyl alcohol in 20 ml of toluene were refluxed under nitrogen for 40 hrs. After evaporation of the solvent, the trapped compound was purified by silica gel column chromatography, eluting with (9:1) dichloromethane-ethyl acetate, to give 2.0 g of the title compound.

EXAMPLE 66

4β-(1-Hydroxymethyl)-vinylthio-3α-(1-p-nitrobenzyloxycarbonyloxyethyl)-1-(1-methoxycarbonyl-2-methyl-1-propenyl)-azetidin-2-one-S-oxide Reaction (3)–(4)

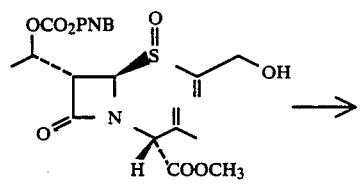

2.0 g of 4β-(1-hydroxymethyl)-vinylthio-3α-(1-p-nitrobenzyloxycarbonyloxyethyl)-1-(1-methoxycarbonyl-2-methyl-2-propenyl)-azetidin-2-one-S-oxide, dissolved in 50 ml of dichloromethane, were left at room temperature in the presence of a few drops of triethylamine for 12 hrs. After evaporating the solvent, the pure title compound was recovered in quantitative yield.

EXAMPLE 67

4β-(1-Bromomethyl)-vinylthio-3α-(1-p-nitrobenzyloxycarbonyloxyethyl)-1-(1-methoxycarbonyl-2-methyl-1-propenyl)-azetidin-2-one Reaction (4)–(12)

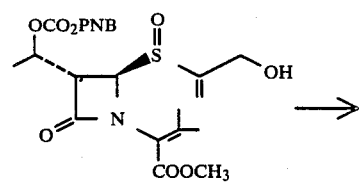

2.0 g of the compound prepared in Example 66 were dissolved in 50 ml of dimethylformamide. After cooling at −20° C., 0.7 ml of pyridine and 3.2 ml of PBr3 were added and the reaction mixture was maintained under stirring for 15 minutes. Ethyl acetate was added to the mixture and the organic phase was shaked with a NaHCO3 saturated solution, washed with water and finally dired over Na2SO4. After evaporating the solvent, 1.7 g of pure title compound were obtained.

EXAMPLE 68

4β-[1-(5-Methyl-1-3,4-thiadiazol-2-yl)-thiomethyl]-vinylthio-3α-(1-p-nitrobenzyloxycarbonyloxyethyl)-1-(1-methoxycarbonyl-2-methyl-1-propenyl)-azetidin-2-one

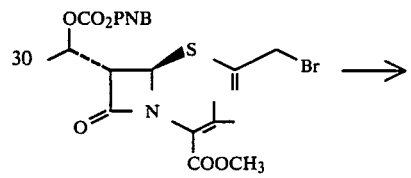

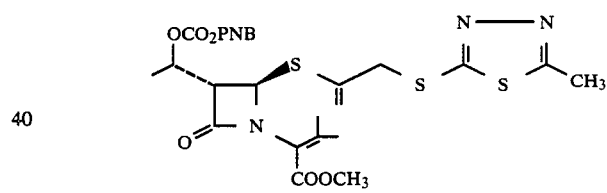

1.8 g of the compound prepared in Example 67 were dissolved in 30 ml of tetrahydrofuran. The resulting solution was cooled at 0° C.; 1.1 g of 5-methyl-1,3,4-thiadiazol-2-thiol sodium salt were added and the mixture was maintained under stirring for 4 hrs. After filtration of the insolubles, the remaining solution was diluted with ethyl acetate, washed with water, dried over Na2SO4, and evaporated: 2 g of the title compound were obtained.

EXAMPLE 69

4β-[1-(1,2,3-Triazol-5-yl)-thiomethyl]-vinylthio-3α-(1-p-nitrobenzyloxycarbonyloxyethyl)-1-(1-methoxycarbonyl-2-methyl-1-propenyl)-azetidin-2-one

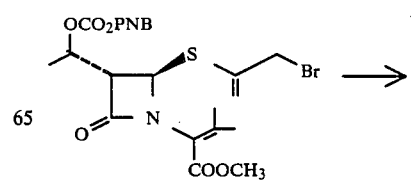

-continued

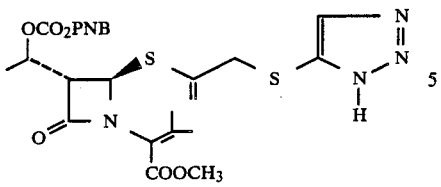

Starting from 2.5 g of the compound prepared in Example 67 and operating as in Example 68, but using 1,2,3-triazol-5-thiol sodium salt, 2.2 g of the title compound were obtained.

EXAMPLE 70

4β-[1-(5-Methyl-1,3,4-thiadiazol-2-yl)]-thioacetylthio-3α-(1-p-nitrobenzyloxycarbonyloxyethyl)-1-methoxy-oxaloyl-azetidin-2-one

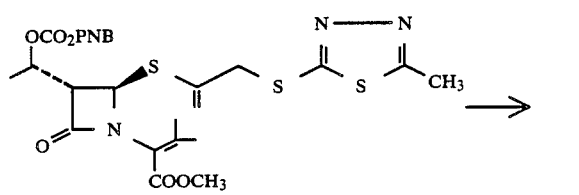

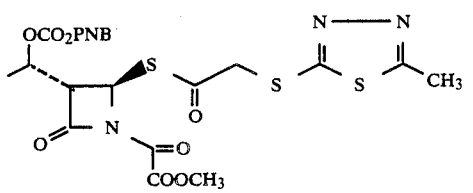

2 g of the compound prepared in Example 68 were dissolved in 250 ml of dichloromethane and cooled at −78° C. A flow of ozonized oxygen was bubbled through the solution until a blue color results. A few drops of P(OCH₃)₃ were added to the solution and the temperature of the mixture was raised to room temperature. The mixture was evaporated to give 1.5 g of the title compound.

EXAMPLE 71

4β-[1-(1,2,3-Triazol-5-yl)]-thioacetylthio-3α-(1-p-nitrobenzyloxycarbonyloxyethyl)-1-methoxy-oxaloyl-azetidin-2-one Reaction (12)–(13)

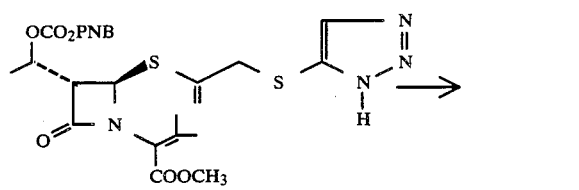

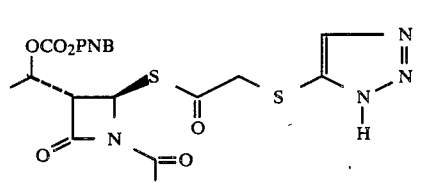

Starting from 1.6 g of the compound prepared in Example 69, and operating as in Example 70, 1.1 g of the title compound were obtained.

EXAMPLE 72

4β-[1-(5-Methyl-1,3,4-thiadiazol-2-yl)]-thioacetylthio-3α-(1-p-nitrobenzyloxycarbonyloxyethyl)-azetidin-2-one Reaction (13)–(14)

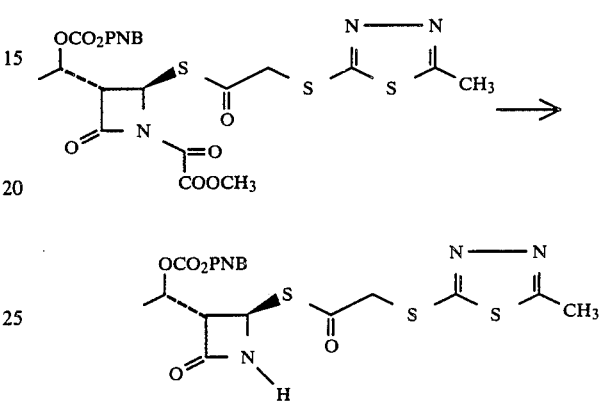

1.5 g of the compound prepared in Example 70 were dissolved in 1 1:1 mixture of methanol and ethyl acetate. A few grams of silica gel were added and the mixture maintained at room temperature under vigorous stirring. After filtering the silica gel, the filtrate was evaporated to give an oil which was chromatographed on silica gel with dichloromethane:ethyl acetate (8:2), giving 0.9 g of pure title compound.

EXAMPLE 73

4β-[1-(1,2,3-Triazol-5-yl)]-thioacetylthio-3α-(1-p-nitrobenzyloxycarbonyloxyethyl)-azetidin-2-one Reaction (13)–(14)

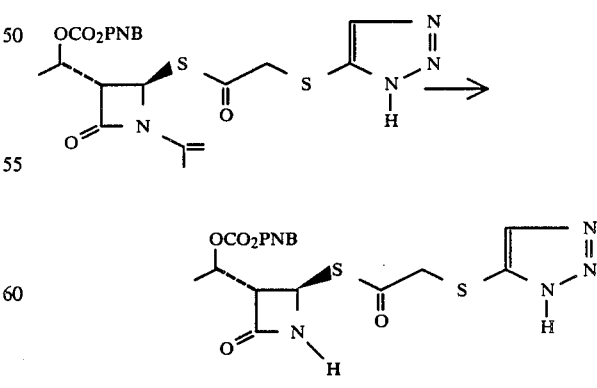

Starting from 1.1 g of the compound prepared in Example 71 and operating as in Example 72, 0.6 g of the title compound were obtained.

EXAMPLE 74

4β-[1-(5-Methyl-1,3,4-thiadiazol-2-yl)]-thioacetylthio-3α-(1-p-nitrobenzyloxycarbonyloxyethyl)-1-(1-acetonyloxycarbonyl-1-hydroxymethyl)-azetidin-2-one Reaction (14)–(15)

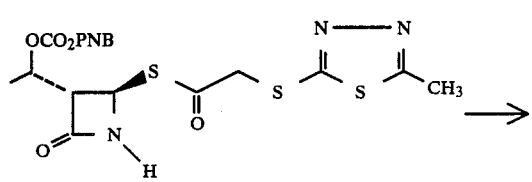

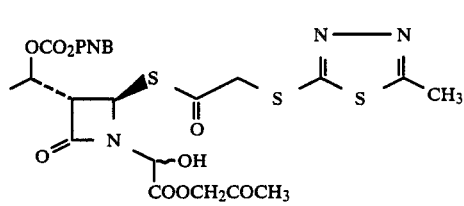

0.9 g of the compound prepared in Example 72 were dissolved in 40 ml of benzene; 0.6 g of acetonyl glyoxylate were added and the resulting solution was refluxed for 3 hrs. After evaporation of the solvent, the crude oil was used for the next step without further purification.

EXAMPLE 75

4β-[1-(1,2,3-Triazol-5-yl)]-thioacetylthio-3α-(1-p-nitrobenzyloxycarbonyloxyethyl)-1-(1-acetonyloxycarbonyl-1-hydroxymethyl)-azetidin-2-one Reaction (14)–(15)

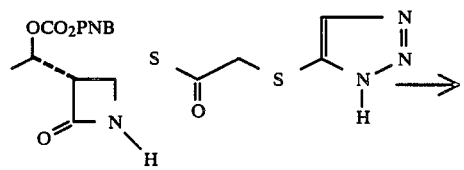

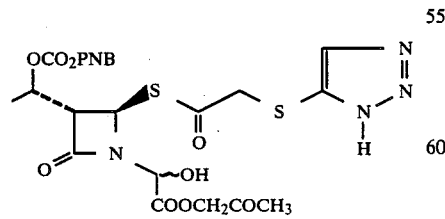

Starting from 0.6 g of the compound prepared in Example 73 and operating as shown in Example 74, 0.7 g of the title compound were obtained.

EXAMPLE 76

4β-[1-(5-Methyl-1,3,4-thiadiazol-2-yl)]-thioacetylthio-3α-(1-p-nitrobenzyloxycarbonyloxyethyl)-1-(1-acetonyloxycarbonyl-1-chloromethyl)-azetidin-2-one Reaction (15)–(16)

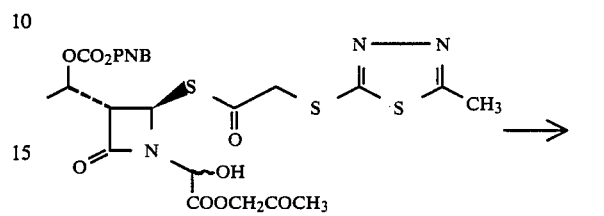

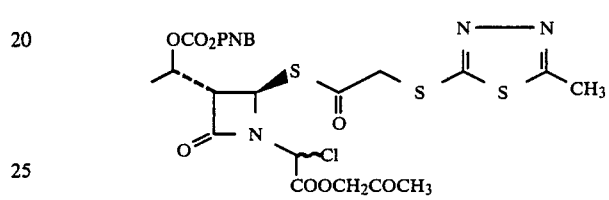

The crude oil obtained in Example 74 was dissolved in anhydrous tetrahydrofuran (30 ml) and cooled at 0° C. Equimolar amounts of pyridine and thionyl chloride were added to the solution until there was a disappearance of the starting material. After filtration of the insoluble material, the filtrate was used immediately for the next step.

EXAMPLE 77

4β-[1-(1,2,3-Triazol-5-yl)]-thioacetylthio-3α-(1-p-nitrobenzyloxycarbonyloxyethyl)-1-(1-acetonyloxycarbonyl-1-chloromethyl)-azetidin-2-one Reaction (15)–(16)

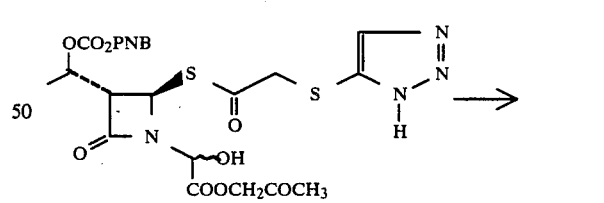

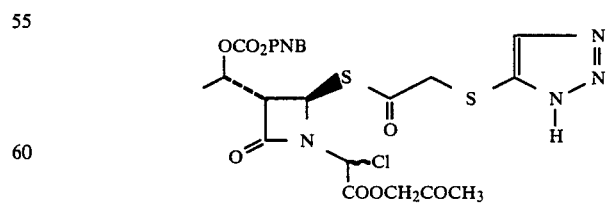

Starting from 0.7 g of the compound prepared in Example 75 and operating as described in Example 74, the crude chloroderivative was obtained. The product was used for the next step without further purification.

EXAMPLE 78

4β-[1-(5-Methyl-1,3,4-thiadiazol-2-yl)]-thioacetylthio-3α-(1-p-nitrobenzyloxycarbonyloxyethyl)-1-(1-acetonyloxycarbonyl-1-triphenylphosphoranylidenemethyl)-azetidin-2-one Reaction (16)–(11)

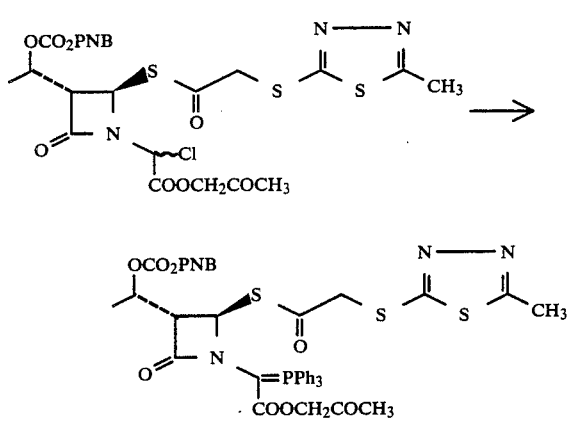

Crude product obtained in Example 76 was dissolved in 20 ml of tetrahydrofuran; 700 mg of triphenylphosphine and 0.35 ml of pyridine were added and the resulting solution was warmed under nitrogen at 70° C. for a few hours. The title phosphorane was purified on silica gel by eluting with dichloromethane:ethyl acetate (1:1). There was obtained 0.6 g of the title compound.

EXAMPLE 79

4β-[1-(1,2,3-Triazol-5-yl)]-thioacetylthio-3α-(1-p-nitrobenzyloxycarbonyloxyethyl)-1-(1-acetonyloxycarbonyloxyethyl-1-triphenylphoshoranylidenemethyl)-azetidin-2-one Reaction (16)–(11)

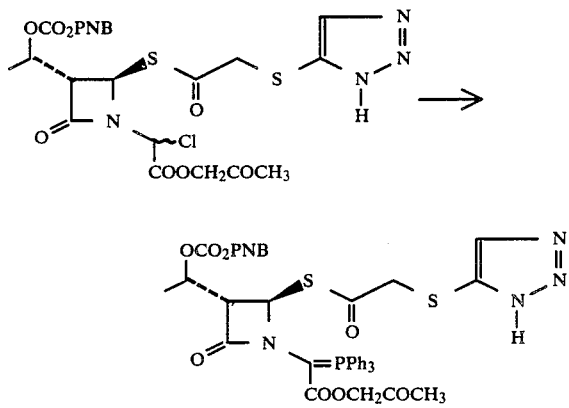

Starting from the crude chloroderivative obtained in Example 77 and operating as illustrated in Example 78, 0.55 g of the title compound were obtained.

EXAMPLE 80

(5R)-Acetonyl-2-[(5-methyl-1,3,4-thiadiazol-2-yl)-thiomethyl]-6α-(1-p-nitrobenzyloxycarbonyloxyethyl)-2-penem-3-carboxylate Reaction (11)–(1)

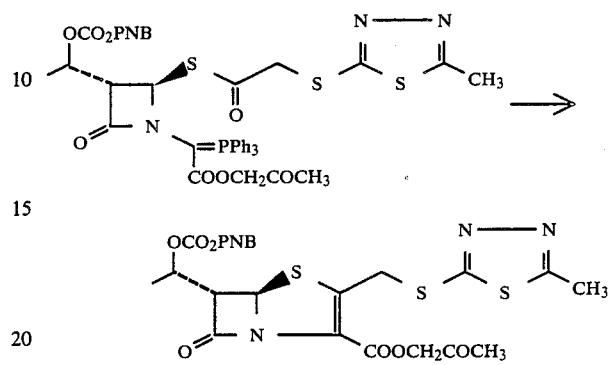

0.6 g of the compound prepared in Example 78 were dissolved in 50 ml of toluene and refluxed under nitrogen for three hours. The title compound was purified by short column chromatography on silica gel eluting with dichloromethane:ethyl acetate (8:2). There was obtained 0.25 g of the title compound. I.R.: 1795, 1750, 1720.

EXAMPLE 81

(5R)-Acetonyl-2-[(1,2,3-triazol-5-yl)-thiomethyl]-6α-(1-p-nitrobenzyloxycarbonyloxyethyl)-2-penem-3-carboxylate Reaction (11)–(1)

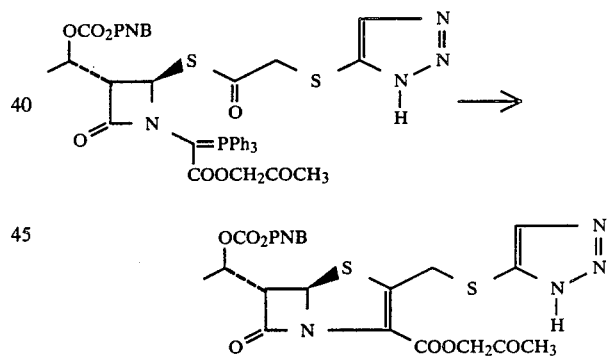

Starting from 0.45 g of the compound prepared in Example 79 and operating as shown in Example 80, 0.180 g of the title compound were obtained.
I.R.: 1795, 1750, 1720.

EXAMPLE 82

(5R)-Acetonyl-2-[(5-methyl-1,3,4-thiadiazol-2-yl)-thiomethyl]-6α-(1-hydroxyethyl)-2-penem-3-carboxylate Reaction (1)

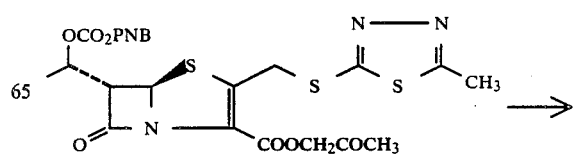

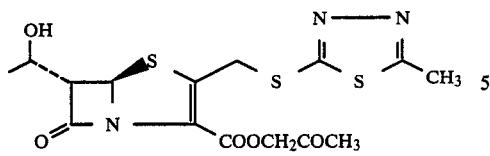

0.450 g of the compound prepared in Example 80 were dissolved in 25 ml of acetonitrile containing a few drops of ethanol and hydrogenated over 10% Pd on carbon (400 mg). The catalyst was removed by filtration and the filtrate was chromatographed on silica gel eluting with dichloromethane:ethyl acetate (7:3), giving 0.18 g of the title compound.

I.R.: 3605, 1795, 1745, 1720.

EXAMPLE 83

(5R)-Acetonyl-2-[(1,2,3-triazol-5-yl)-thiomethyl]-6α-(1-hydroxyethyl)-2-penem-3-carboxylate Reaction (1)

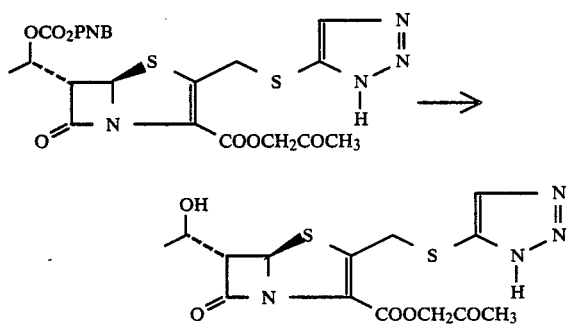

Starting from 0.380 g of the compound prepared in Example 81 and operating as in Example 82, 0.12 g of the title compound were obtained.

I.R.: 3610, 1795, 1750, 1720.

EXAMPLE 84

(5R)-2[(5-Methyl-1,3,4-thiadiazol-2-yl)-thiomethyl]-6α-(1-hydroxymethyl)-2-penem-3-carboxylic acid Reaction (1)

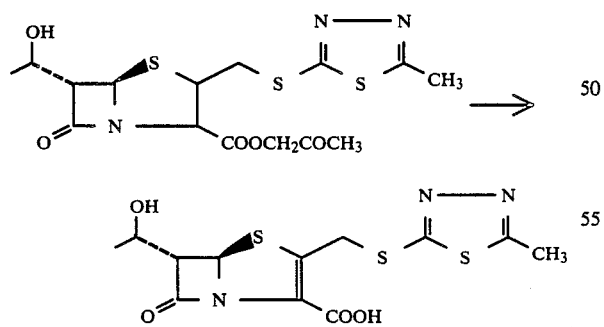

A solution of 0.200 g of the compound prepared in Example 82 in acetonitrile (30 ml) containing a few drops of water was cooled at 0° C.; 5 ml of a 0.1N NaOH solution were added under nitrogen and the solution was stirred for 10 minutes. The alkaline mixture was extracted twice with methylene chloride, acidified with a 10% citric acid aqueous solution, and extracted again twice with methylene chloride. The combined organic phases were dried over $Na_2SO_4$ and evaporated giving 0.110 g of the title compound.

I.R.: 3500, 1795, 1665.

EXAMPLE 85

(5R)-2-[(1,2,3-Triazol-5-yl)-thiomethyl]-6α-(1-hydroxyethyl)-2-penem-3-carboxylic acid Reaction (1)

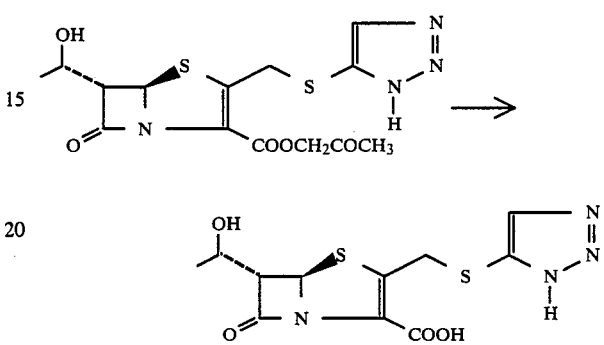

Starting from 0.25 g of the compound prepared in Example 83 and operating as shown in Example 84, 0.135 g of the title compound were obtained.

I.R.: 3490, 1795, 1660.

EXAMPLE 86

4β-(1-Carbamoyloxymethyl)-vinylthio-3α-(1-p-nitrobenzyloxycarbonyloxyethyl)-1-(1-methoxycarbonyl-2-methyl-1-propenyl)azetidin-2-one-S-oxide Reaction (4)–(5)

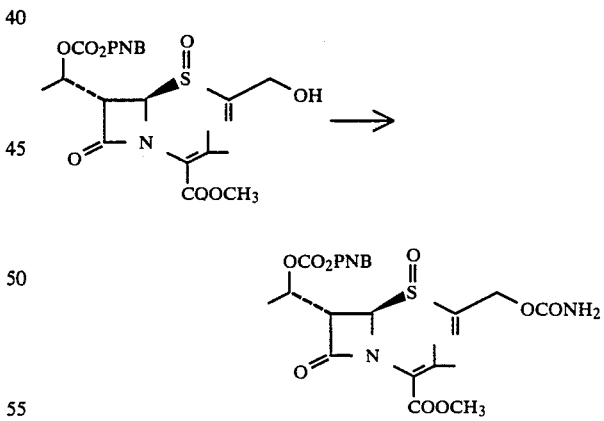

2.2 g of the compound prepared in Example 66 were dissolved in 30 ml of acetonitrile and cooled at 0° C. Then 0.8 ml of chlorosulphonyl isocyanate were added under nitrogen and the mixture was stirred for 2 hours. The reaction mixture was poured into a saturated NaHCO$_3$ solution, stirred for a few minutes, and then extracted with ethyl acetate. After drying over $Na_2SO_4$, evaporation of the solvent gave 1.5 g of the title compound.

EXAMPLE 87

4β-(1-Carbamoyloxymethyl)-vinylthio-3α-(1-p-nitrobenzyloxycarbonyloxyethyl)-1-(1-methoxycarbonyl-2-methyl-1-propenyl)-azetidin-2-one Reaction (4)–(12)

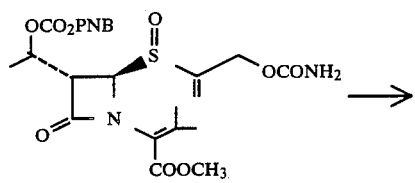

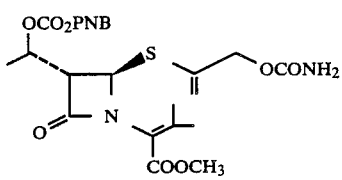

Starting from 1.7 g of the compound prepared in Example 86 and operating as in Example 67, 1.4 g of the title compound were obtained.

EXAMPLE 88

4β-(1-Carbamoyloxy)-acetylthio-3α-(1-p-nitrobenzyloxycarbonyloxyethyl)-1-methoxyoxaloyl-azetidin-2-one Reaction (12)–(13)

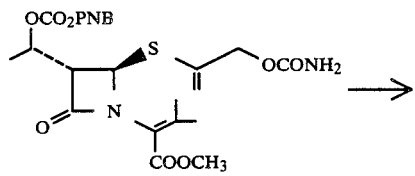

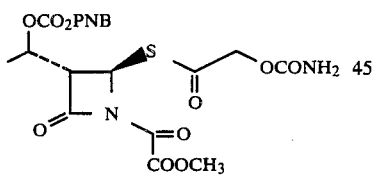

Starting from 2.2 g of the compound prepared in Example 87 and operating as illustrated in Example 70, 1.4 g of the title compound were obtained.

EXAMPLE 89

4β-(1-Carbamoyloxy)-acetylthio-3α-(1-p-nitrobenzyloxycarbonyloxyethyl)-azetidin-2-one Reaction (13)–(14)

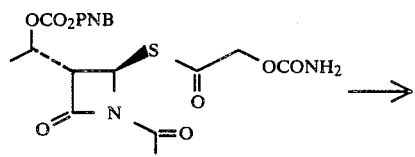

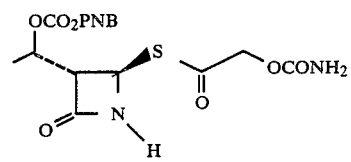

Starting from 1.4 g of the compound prepared in Example 88 and operating as shown in Example 72, 0.9 g of the title compound were obtained.

EXAMPLE 90

4β-(1-Carbamoyloxy)-acetylthio-3α-(1-p-nitrobenzyloxycarbonyloxyethyl)-1-(1-acetonyloxycarbonyl-1-hydroxymethyl)-azetidin-2-one Reaction (14)–(15)

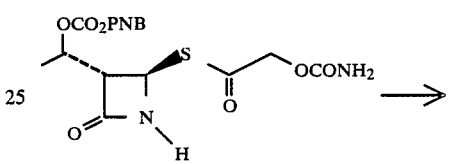

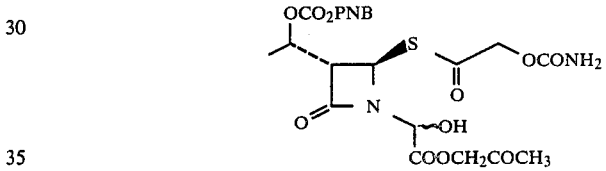

Starting from 0.9 g of the compound prepared in Example 89 and 0.6 g of acetonyl glyoxylate and operating as in Example 74, the crude carbinolamide was obtained.

EXAMPLE 91

4β-(Carbamoyloxy)-acetylthio-3α-(1-p-nitrobenzyloxycarbonyloxyethyl)-1-(1-acetonyloxycarbonyl-1-chloromethyl)-azetidin-2-one Reaction (15)–(16)

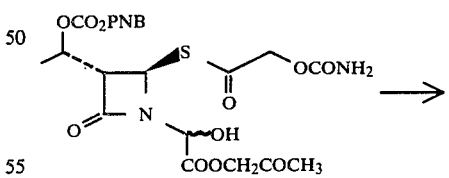

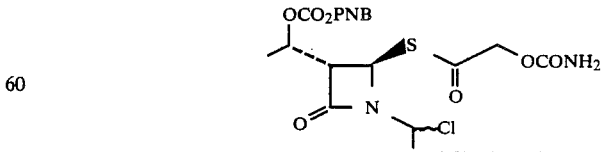

Starting from the crude product obtained in Example 90 and operating as in Example 76, the crude chloroderivative was obtained.

EXAMPLE 92

4β-(1-Carbamoyloxy)-acetylthio-3α-(1-p-nitrobenzyloxycarbonyloxyethyl)-1-(1-acetonyloxycarbonyl-1-triphenylphosphoranylidenemethyl-1)-azetidin-2-one Reaction (16)–(11)

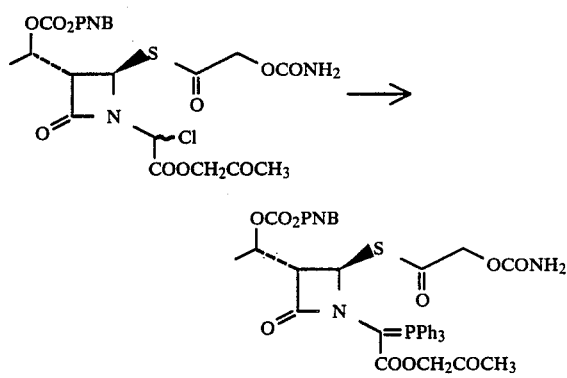

Starting from the crude product obtained in Example 91 and operating as in Example 78, 0.40 g of the phosphorane were obtained.

EXAMPLE 93

(5R)-Acetonyl-2-carbamoyloxymethyl-6d-(1-p-nitrobenzyloxycarbonyloxyethyl)-2-penem-3-carboxylate Reaction (11)–(1)

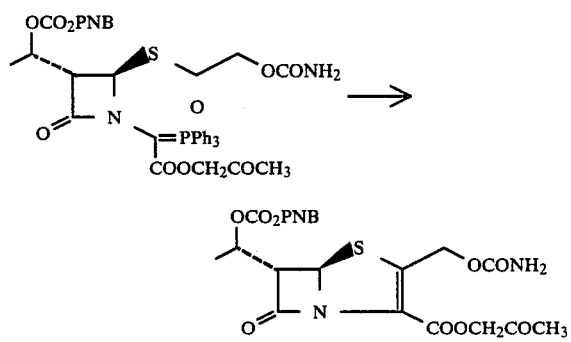

Starting from 0.4 g of the compound prepared in Example 92 and operating as in Example 80, 0.11 g of the title compound were obtained.

EXAMPLE 94

(5R)-Acetonyl-2-carbamoyloxymethyl-6d-(1-hydroxyethyl)-2-penem-3-carboxylate Reaction (1)

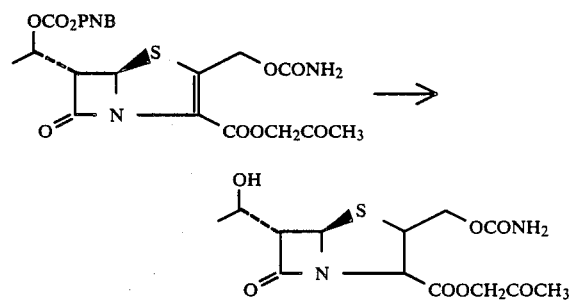

Starting from 0.35 g of the compound prepared in Example 93 and operating as in Example 82, 0.11 g of the title compound were obtained.

EXAMPLE 95

(5R)-2(Carbamoyloxymethyl)-6α-(1-hydroxyethyl)-2-penem-3-carboxylic acid Reaction (1)

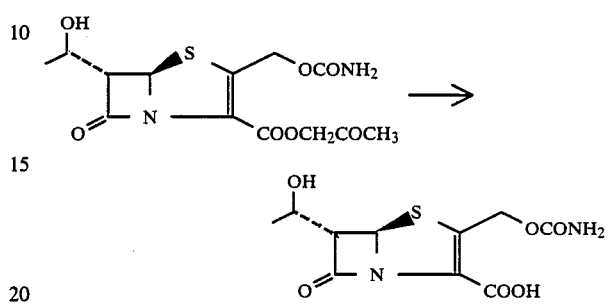

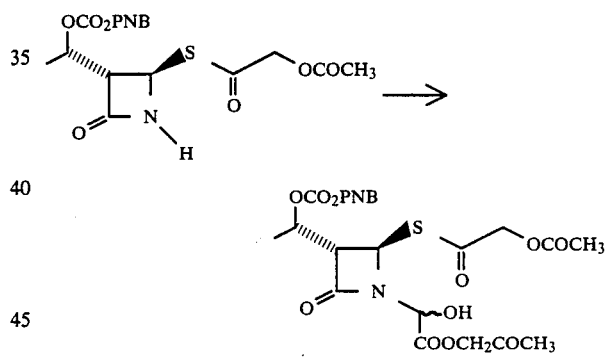

Starting from 0.11 g of the compound prepared in Example 94 and operating as in Example 84, 0.060 g of the title compound were obtained.
I.R.: 3400–3500, 1795, 1700–1650.

EXAMPLE 96

(a)

4β-Acetylglycolylthio-3α-[1-p-nitrobenzyloxycarbonyloxymethyl]-1-[1-acetonyloxycarbonyl-1-hydroxymethyl]-azetidin-2-one Reaction (14)–(15)

A solution of 1.04 g of 4β-acetylglycolylthio-3α-[1-p-nitrobenzyloxycarbonyloxyethyl]-azetidin-2-one, prepared according to Example 46, and 1.8 g of acetonyl glyoxylate in 20 ml of benzene was refluxed for 4 hours. Evaporation of the solvent gave the crude title compound which was used for the next step without further purification.

(b)

4β-Acetylglycolylthio-3α-[1-p-nitrobenzyloxycarbonyloxyethyl]-1-[1-acetonyloxycarbonyl-1-chloromethyl]-azetidin-2-one Reaction (15)–(16)

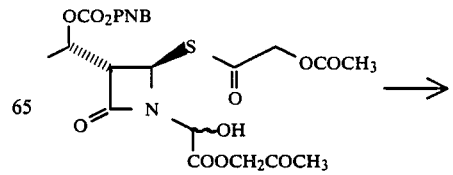

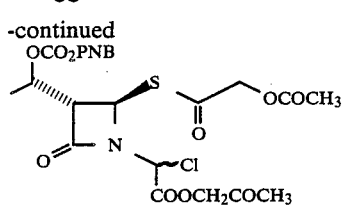

The crude carbinolamide obtained from the step (a) was dissolved in 20 ml of anhydrous tetrahydrofuran and cooled at 0° C. Equimolar amounts of pyridine and thionyl chloride were added until all starting material disappeared. The precipitate was filtered; evaporation of the filtrate gave the crude title compound which was used for the next step without further purification.

(c)
4β-Acetylglycolylthio-3α-(1-p-nitrobenzyloxycarbonyloxyethyl]-1-[acetonyloxycarbonyl-1-triphenylphosphoranylidenemethyl]-azetidin-2-one Reaction (16)–(11)

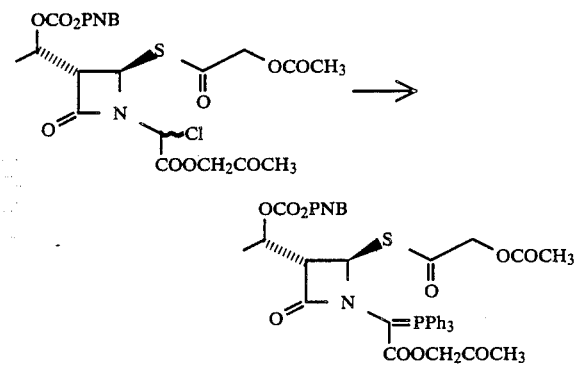

The crude chloroderivative was dissolved in 100 ml of methylene chloride; 1.5 g of triphenylphosphine and 10 g of silica gel were added and the solvent evaporated under vacuum. The solid material was left overnight at room temperature, poured into a column chromatograph and eluted with 1:1 methylene ethyl acetate, giving 1.5 g of the title compound.

(d)
(5R)-Acetonyl-6α-[1-p-nitrobenzyloxycarbonyloxyethyl]-2-acetoxymethyl-2-penem-3-carboxylate Reaction (11)–(1)

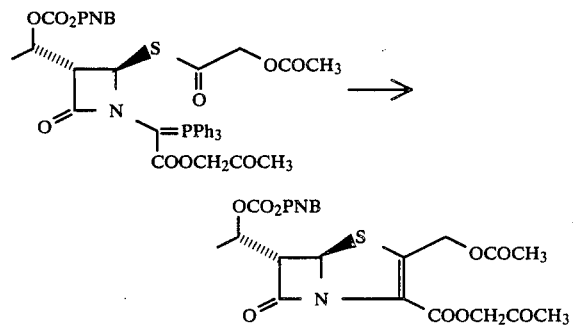

1.5 g of 4β-acetylglycolylthio-3-[1-p-nitrobenzyloxycarbonyloxyethyl]-1-[acetonyloxycarbonyl-1-triphenylphosphoranylidenemethyl]-azetidin-2-one were dissolved in 50 ml of toluene and refluxed for three hours. Evaporation of the solvent gave an oil which was purified by short column chromatography on silica gel eluting with (9:1) dichloromethane-ethyl acetate. There was obtained 0.51 g of the title compound.

Erithro

PMR (CDCl₃):
1.46 (d, J=6.5 Hz, 3H, C$H_3$CH)
2.07 (s, 3H, OCOC$H_3$) Pl 2.16 (s, 3H, COC$H_3$)
4.02 (dd, J=2.0, 4.0 Hz, 1H, H—6)
4.73 (s, 2H, C$H_2$CO)
5.0–5.3 (m, 1H, CHO)
5.12, 5.38 (dd, J=15.5 Hz, 2H, C$H_2$OCO)
5.22 (s, 2H, COC$H_2$Ph)
7.4–8.5 (m, 4H, PhNO₂).

IR (CHCl₃)
1725 cm⁻¹ C=O unsaturated esters, ketones;
1750 cm⁻¹ C=O esters;
1800 cm⁻¹ C=O β-lactam.

Threo

PMR (CDCl₃):
1.45 (d, J=6.0 Hz, 3H, C$H_3$CH)
2.08 (s, 3H, OCOC$H_3$)
2.19 (s, 3H, COC$H_3$)
3.96 (dd, J=2.0, 7.0 Hz, 1H, H—6)
4.77 (s, 2H, C$H_2$CO)
5.0–5.4 (m, 1H, CHO)
5.13, 5.42 (d, J=16.0 Hz, C$H_2$OCO)
5.25 (s, 2H, C$H_2$Ph)
5.66 (d, J=2.0 Hz, 1H, H—5)
7.4–8.5 (m, 4H, PhNO₂)

IR (CHCl₃)
1725 cm⁻¹ C=O unsaturated esters, ketones;
1750 cm⁻¹ C=O esters;
1800 cm⁻¹ C=O β-lactam.

EXAMPLE 97

(5R)-Acetonyl-6α-[1-hydroxyethyl]-2-acetoxymethyl-2-penem-3-carboxylate Reaction (1)

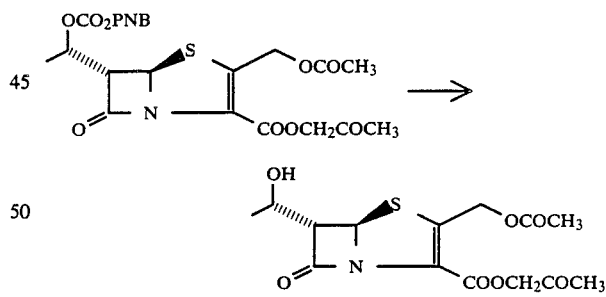

0.51 g of (5R)-acetonyl-6d-[1-p-nitrobenzyloxycarbonyloxyethyl]-2-acetoxymethyl-2-penem-3-carboxylate prepared according to Example 96 were dissolved in 60 ml of a (1:1) acetonitrile:(95%) ethanol mixture. 0.46 g of 10% Pd/C were added and the mixture was stirred under an hydrogen atmosphere for one hour. After filtering the catalyst, the filtrate was evaporated and the title compound purified by silica gel column chromatography eluting with (8:2) dichloromethane-ethyl acetate, giving 0.20 g of pure product.

Erithro

PMR (CDCl₃):
1.38 (d, J=6.5 Hz, 3H, C$H_3$CH);

2.09 (s, 3H, OCOCH₃);
2.20 (s, 3H, COCH₃);
3.86 (dd, J=2.0, 4.0 Hz, 1H, H—6);
4.22 (dq, J=6.5, 4.0 Hz, 1H, CHOH);
4.72 (s, 2H, CH₂CO);
5.12, 5.42 (d, J=15.5 Hz, 2H, CH₂OCO);
5.58 (d, J=2.0 Hz, 1H, H—5).

Threo

PMR (CDCl₃):
1.32 (d, J=6.5 Hz, 3H, CH₃CH);
2.10 (s, 3H, OCOCH₃);
2.20 (s, 3H, COCH₃);
3.06 (bs, 1H, OH);
3.74 (dd, J=2.0, 7.0 Hz, 1H, H—6);
4.23 (m, 1H, CHOH);
4.77 (s, 2H, CH₂CO);
5.12, 5.38 (s, J=16.0 Hz, 2H, CH₂OCO);
5.63 (d, J=20 Hz, 1H, H—5).

EXAMPLE 98

(5)-2-Acetoxymethyl-6-(1-hydroxyethyl)-2-penem-3-carboxylate sodium salt Reaction (1)

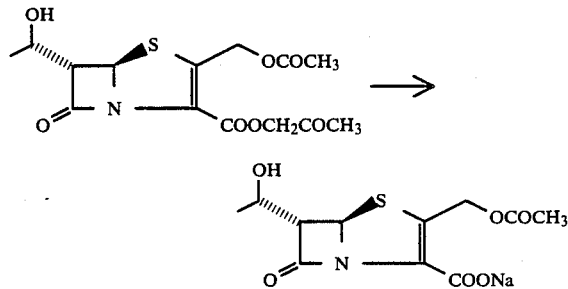

0.21 g of (5R)-acetonyl-6-[1-hydroxyethyl]-2-acetoxymethyl-2-penem-3-carboxylate prepared according to Example 97 were dissolved in 20 ml of acetonitrile and 3 ml of water. The reaction mixture was cooled at 0° C. under nitrogen and 7.4 ml of a 0.1N NaOH aqueous solution were added slowly within 30 minutes. After evaporating acetonitrile under vacuum, the residue was extracted twice with cold ethyl acetate. A C₁₈ reverse phase chromatography (eluting with water) of the concentrated aqueous phase gave 0.054 g of pure title compound.

Erithro

PMR (D₂O)80 mKz:
1.34 (d, J=6.3 Hz, 3H, CH₃CH);
2.14 (s, 3H, OCOCH₃);
4.01 (m, 1H, H—6);
4.22 (m, 1H, CHOH);
5.10, 5.44 (d, J=14.0 Hz, 2H, CH₂OCO);
5.63 (d, J=1.0 Hz, 1H, H—5).

U.V. (ethanol 95%):
λ max 262 nm(ε2000), 308 nm (ε2520) [α]$_D$=128
(C=O 0.92, H₂O).

Threo

PMR (D₂O):
1.31 (d, J=6.5 Hz, 3H, CH₃.CH)
2.19 (w, 3H, OCOCH₃)
3.92 (dd, J=1.5, 7.0 Hz, 1H, H—6)
4.21 (m, 1H, CHOH)
5.10, 5.44 (d, J=14.0 Hz, 2H, Ch₂OCO)
5.67 (d, J=1.5 Hz, 1H, H—5).

U.V. (ethanol 95%):
γ max 262 nm(ε3410), 308 nm (ε4340).

What is claimed is:

1. A compound of the formula:

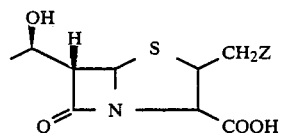

wherein R is a hydrogen atom, $C_1$-$C_5$-alkyl; 2,2,2-trichloroethyl p-nitrobenzyl, acetonyl, or acetoxymethyl; Z is selected from the group consisting of pyridinium, and OCOC₁—C₅-alkyl, and a pharmaceutically acceptable salt thereof.

2. The compound of claim 1 which is (5R)-2-acetoxymethyl-6-(1-hydroxyethyl)-2-penem-3-carboxylic acid.

3. The compound of claim 1 which is (5R)-acetonyl-6α-[1-hydroxyethyl]-2-acetoxymethyl-2-penem-3-carboxylate.

4. The compound of claim 1 which is (5R)-2-acetoxymethyl-6-(1-hydroxyethyl)-2-penem-3-carboxylate sodium salt.

5. The treatment of infectious diseases, said treatment comprising administering to a host in need of such treatment a therapeutically effective amount of a compound of claim 1 or of a pharmaceutically acceptable salt thereof.

6. A pharmaceutical composition comprising an antibacterially effective amount of a compound of claim 1, or a pharmaceutically acceptable salt thereof in admixture with a pharmaceutically acceptable diluent or carrier.

* * * * *

UNITED STATES PATENT AND TRADEMARK OFFICE
CERTIFICATE OF CORRECTION

PATENT NO. : 4,558,042

DATED : December 10, 1985

INVENTOR(S) : Maurizio Foglio et al.

It is certified that error appears in the above-identified patent and that said Letters Patent is hereby corrected as shown below:

In the abstract, delete " 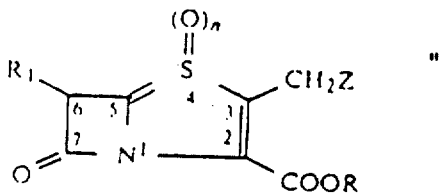 "

and insert

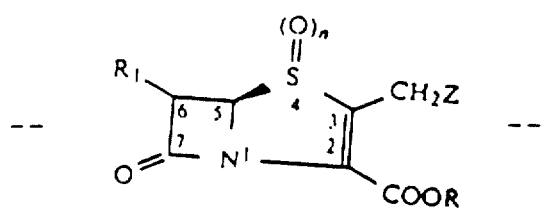

--

IN THE SPECIFICATION

Column 23, line 21, delete " 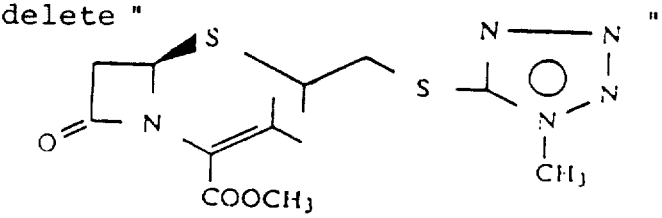 "

and insert

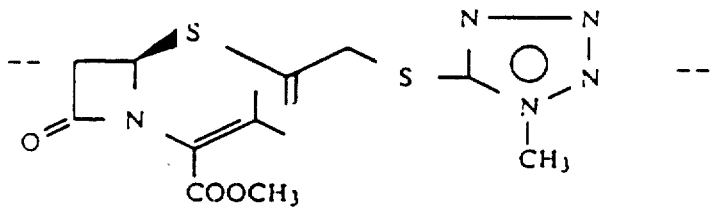 --

UNITED STATES PATENT AND TRADEMARK OFFICE
CERTIFICATE OF CORRECTION

PATENT NO. : 4,558,042

DATED : December 10, 1985

INVENTOR(S) : Maurizio FOGLIO et al.

It is certified that error appears in the above-identified patent and that said Letters Patent is hereby corrected as shown below:

Column 27, line 7, delete " 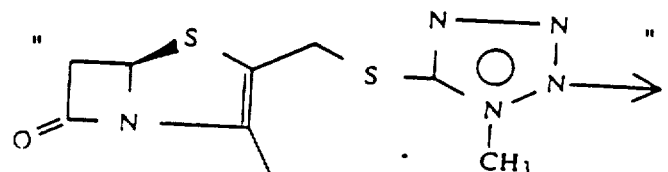 "

and insert

-- 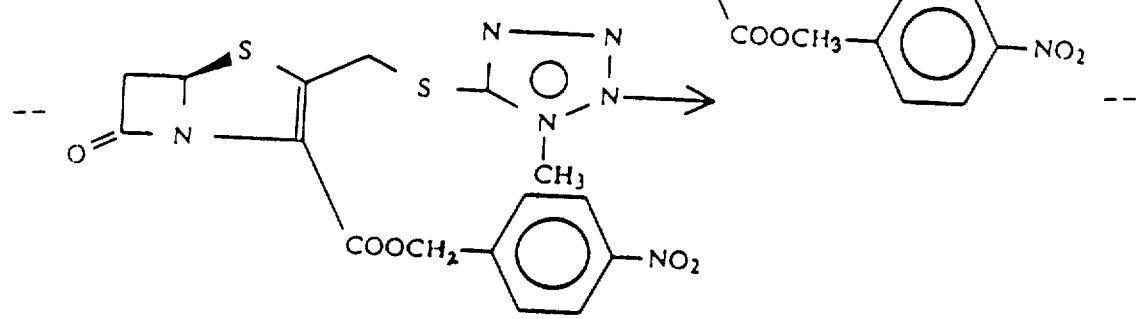 --

Column 27, line 34, delete " 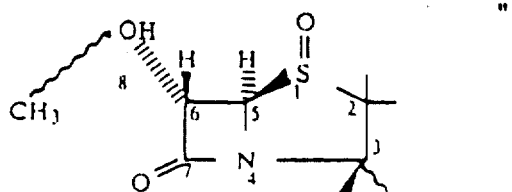 "

and insert

-- 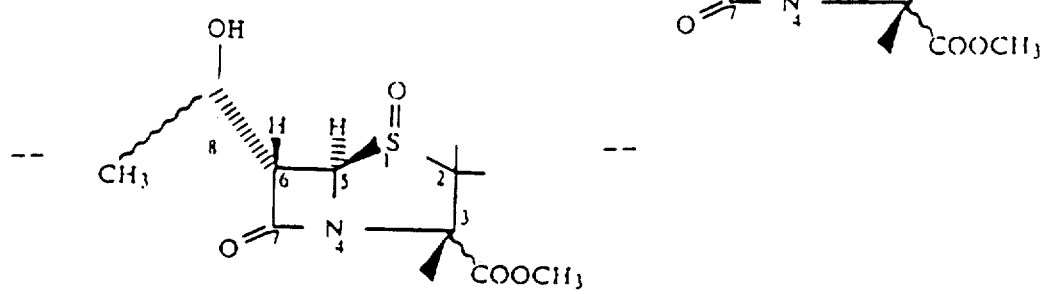 --

UNITED STATES PATENT AND TRADEMARK OFFICE
CERTIFICATE OF CORRECTION

PATENT NO. : 4,558,042

DATED : December 10, 1985

INVENTOR(S) : Maurizio FOGLIO et al.

It is certified that error appears in the above-identified patent and that said Letters Patent is hereby corrected as shown below:

Column 33, line 43, delete " 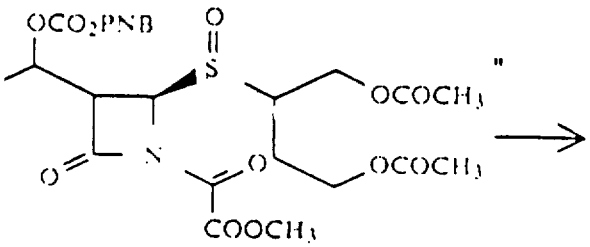 "

and insert

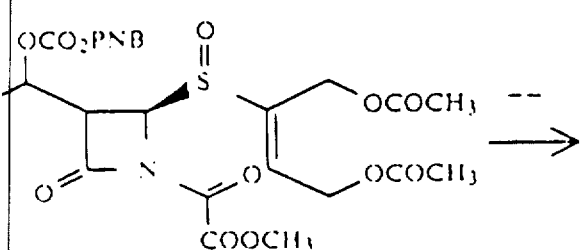

Column 39, line 47, delete " 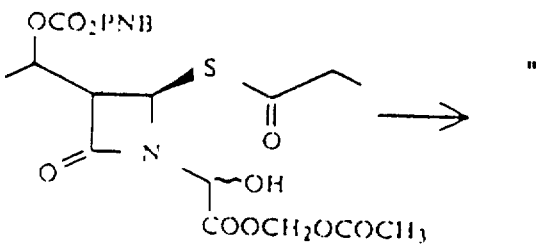 "

and insert 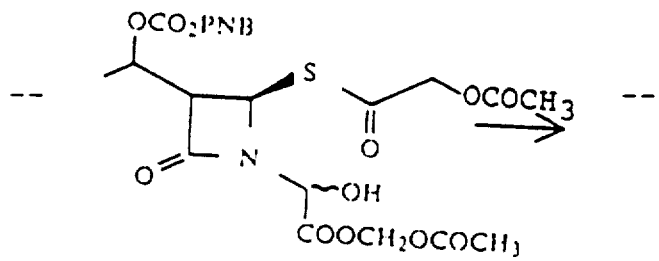

UNITED STATES PATENT AND TRADEMARK OFFICE
CERTIFICATE OF CORRECTION

PATENT NO. : 4,558,042

DATED : December 10, 1985

INVENTOR(S) : Maurizio FOGLIO et al.

It is certified that error appears in the above-identified patent and that said Letters Patent is hereby corrected as shown below:

Column 35, line 3, delete " 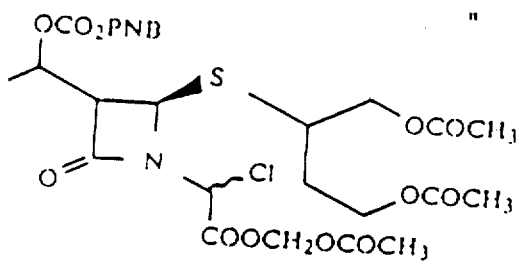 "

and insert

-- 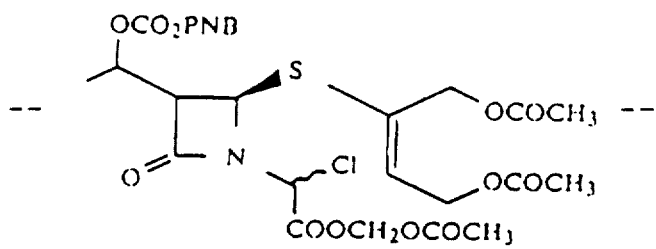 --

Column 40, line 11, delete " 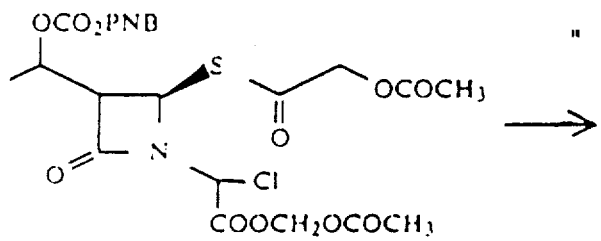 "

and insert

-- 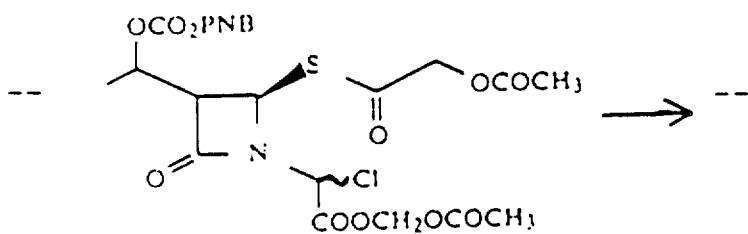 --

UNITED STATES PATENT AND TRADEMARK OFFICE
CERTIFICATE OF CORRECTION

PATENT NO. : 4,558,042

DATED : December 10, 1985

INVENTOR(S) : Maurizio FOGLIO et al.

It is certified that error appears in the above-identified patent and that said Letters Patent is hereby corrected as shown below:

Column 43, line 3, delete " 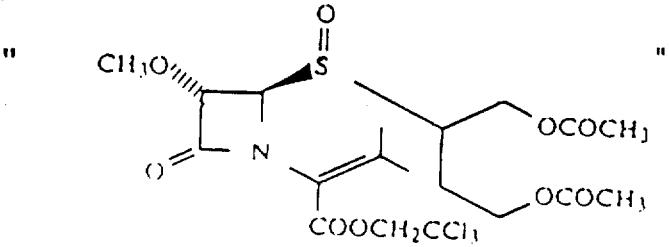 "

and insert

-- 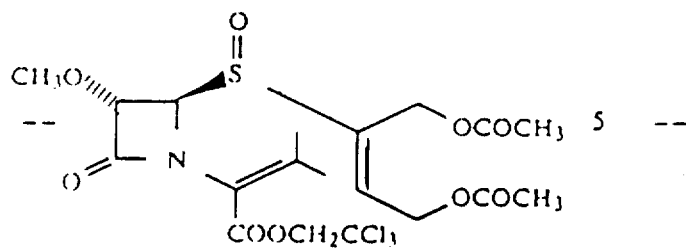 5 --

Column 44, line 3, delete " 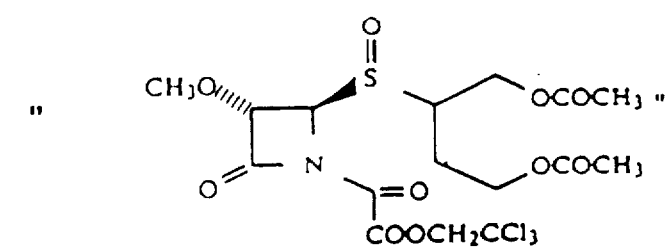 "

and insert

-- 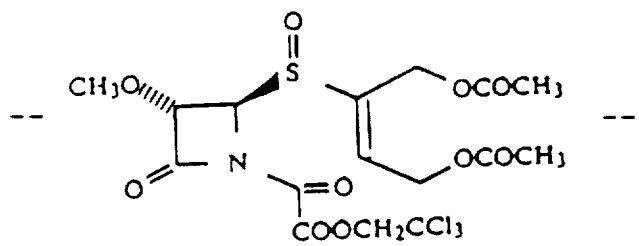 --

UNITED STATES PATENT AND TRADEMARK OFFICE
CERTIFICATE OF CORRECTION

PATENT NO. : 4,558,042

DATED : December 10, 1985

INVENTOR(S) : Maurizio FOGLIO et al.

It is certified that error appears in the above-identified patent and that said Letters Patent is hereby corrected as shown below:

Column 45, line 12, delete " 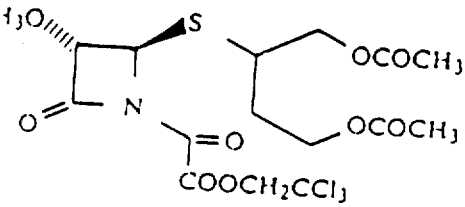 "  → and insert -- 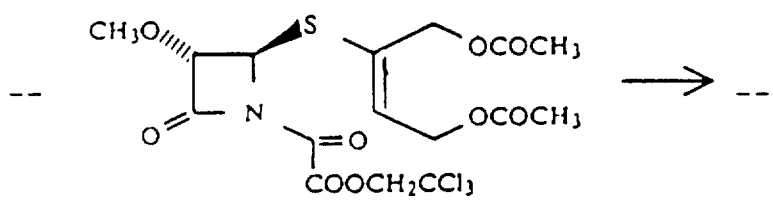 --

Column 48, line 15, delete " 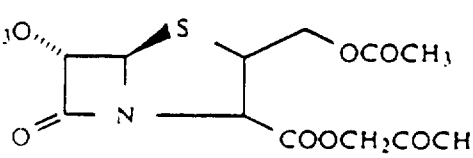 "

and insert -- 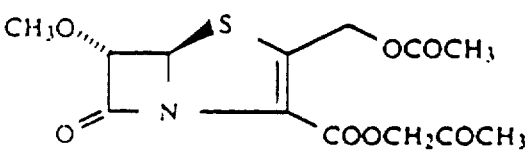 --

UNITED STATES PATENT AND TRADEMARK OFFICE
CERTIFICATE OF CORRECTION

PATENT NO. : 4,558,042    Page 7 of 9
DATED : December 10, 1985
INVENTOR(S) : Maurizio FOGLIO et al.

It is certified that error appears in the above-identified patent and that said Letters Patent is hereby corrected as shown below:

Column 57, line 47, " 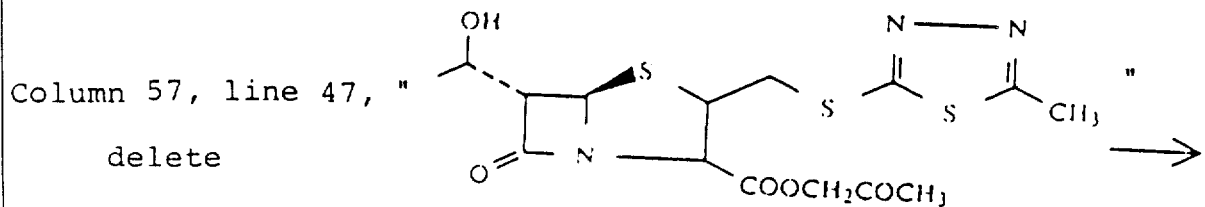 "

delete and insert -- 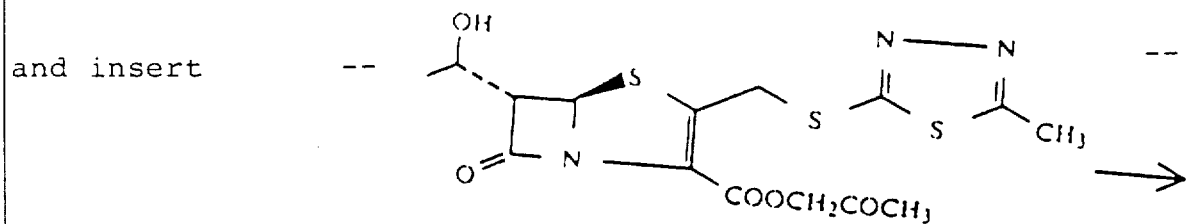 --

Column 61, line 35, delete " 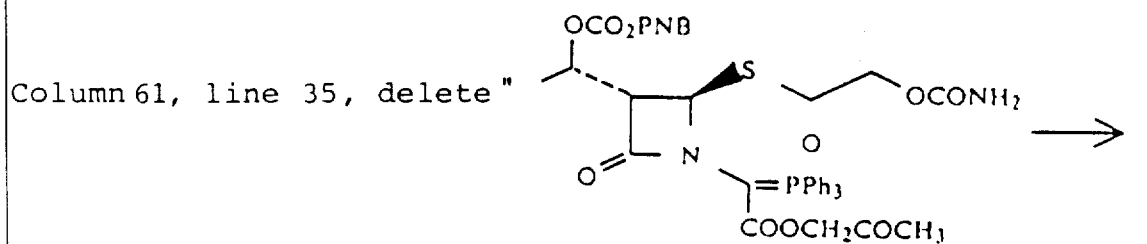 "

and insert -- 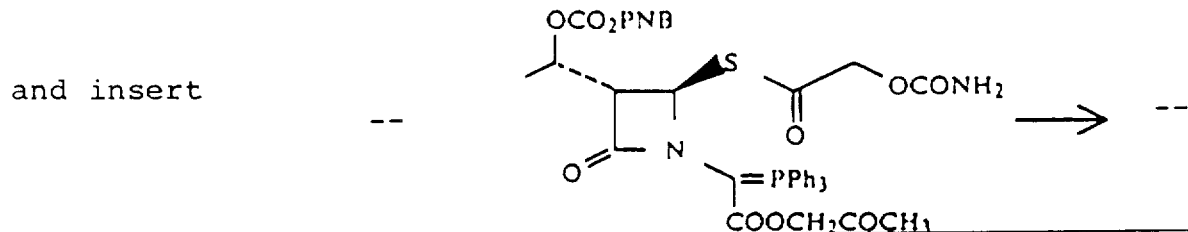 --

UNITED STATES PATENT AND TRADEMARK OFFICE
CERTIFICATE OF CORRECTION

PATENT NO. : 4,558,042

DATED : December 10, 1985

INVENTOR(S) : Maurizio Foglio et al.

It is certified that error appears in the above-identified patent and that said Letters Patent is hereby corrected as shown below:

Column 61, line 57, delete " 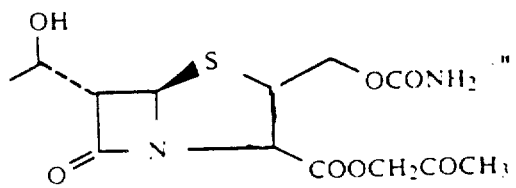 "

and insert -- 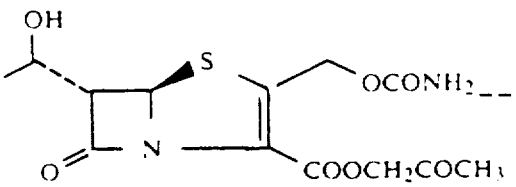 --

UNITED STATES PATENT AND TRADEMARK OFFICE
CERTIFICATE OF CORRECTION

PATENT NO. : 4,558,042

DATED : December 10, 1985

INVENTOR(S) : Maurizio Foglio et al.

It is certified that error appears in the above-identified patent and that said Letters Patent is hereby corrected as shown below:

Claim 1, line 2, delete 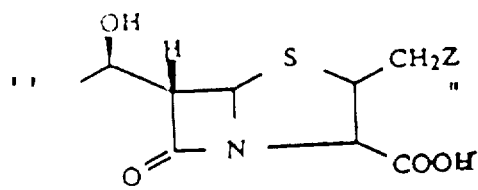

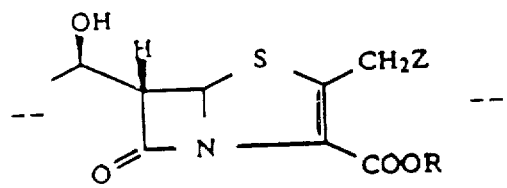

Signed and Sealed this

Tenth Day of November, 1987

Attest:

DONALD J. QUIGG

*Attesting Officer*   *Commissioner of Patents and Trademarks*